(12) United States Patent
Mir et al.

(10) Patent No.: US 8,231,788 B2
(45) Date of Patent: Jul. 31, 2012

(54) METHOD AND APPARATUS FOR THE FILTRATION OF BIOLOGICAL SAMPLES

(75) Inventors: Leon Mir, Brookline, MA (US); Gaston de los Reyes, Somerville, MA (US)

(73) Assignee: SPF Innovations, LLC, Sommerville, MA (US)

( * ) Notice: Subject to any disclaimer, the term of this patent is extended or adjusted under 35 U.S.C. 154(b) by 367 days.

(21) Appl. No.: 12/371,611

(22) Filed: Feb. 15, 2009

(65) Prior Publication Data
US 2009/0145845 A1    Jun. 11, 2009

Related U.S. Application Data

(63) Continuation of application No. 11/615,031, filed on Dec. 22, 2006, now Pat. No. 7,510,654.

(60) Provisional application No. 60/755,009, filed on Dec. 29, 2005, provisional application No. 60/754,813, filed on Dec. 29, 2005.

(51) Int. Cl.
  *B01D 61/00* (2006.01)
  *B01D 63/00* (2006.01)
  *B01D 35/00* (2006.01)

(52) U.S. Cl. .............. 210/651; 210/257.2; 210/321.74; 210/90; 210/321.75; 422/535

(58) Field of Classification Search .......... 210/321, 210/75, 7, 74, 76, 6, 321.72, 195.2, 257, 210/2, 261, 321.75, 321.74, 90; 422/99–10, 422/48, 535
See application file for complete search history.

(56) References Cited

U.S. PATENT DOCUMENTS

| 4,200,533 A |   | 4/1980  | Gaddis et al.   |         |
|-------------|---|---------|-----------------|---------|
| 4,261,834 A | * | 4/1981  | deWinter        | 210/651 |
| 4,343,705 A |   | 8/1982  | Legg            |         |
| 4,578,191 A |   | 3/1986  | Jaffrin et al.  |         |
| 4,639,316 A |   | 1/1987  | Eldegheidy      |         |
| 4,668,399 A |   | 5/1987  | Duggins         |         |
| 4,690,754 A |   | 9/1987  | Koyama et al.   |         |
| 4,716,044 A |   | 12/1987 | Thomas et al.   |         |
| 4,734,192 A |   | 3/1988  | Champion et al. |         |

(Continued)

FOREIGN PATENT DOCUMENTS
EP    1 198 544 B1    3/2004

OTHER PUBLICATIONS

Coulter (R) CellPrep Sample Preparation Systems, http://www.beckmancoulter.com/products/instrument/flowcytometry/cellprep.asp, date unknown, viewed on Mar. 18, 2007.

(Continued)

*Primary Examiner* — Ana Fortuna
(74) *Attorney, Agent, or Firm* — Barry Gaiman

(57) ABSTRACT

A separation module and method are disclosed for processing a liquid sample and providing high conversion by operating a single-pass tangential-flow process without a recirculation loop. In one embodiment, the separation module includes three reservoirs and has at least one long, thin channel with a large ratio of channel membrane area to: channel void volume; volume of a sample feed reservoir; and volume of the feed sample. In another embodiment, the separation module includes two reservoirs and a hydrophobic vent. The single-pass process provides high conversion while operating with relatively low pressure sources.

20 Claims, 15 Drawing Sheets

U.S. PATENT DOCUMENTS

| | | | | |
|---|---|---|---|---|
| 4,761,230 | A | 8/1988 | Pacheco et al. | |
| 4,786,482 | A * | 11/1988 | The et al. | 423/130 |
| 4,879,098 | A | 11/1989 | Oberhardt et al. | |
| 4,906,372 | A * | 3/1990 | Hopkins | 210/321.74 |
| 5,597,486 | A | 1/1997 | Lutz | |
| 5,601,711 | A | 2/1997 | Sklar et al. | |
| 5,647,990 | A | 7/1997 | Vassarotti | |
| 5,674,395 | A | 10/1997 | Stankowski et al. | |
| 5,685,980 | A * | 11/1997 | Patapoff et al. | 210/244 |
| 5,698,161 | A | 12/1997 | Montoya | |
| 5,762,789 | A * | 6/1998 | de los Reyes et al. | 210/321.75 |
| 5,792,425 | A | 8/1998 | Clark et al. | |
| 5,851,491 | A * | 12/1998 | Moulton | 422/101 |
| 5,922,210 | A | 7/1999 | Brody et al. | |
| 5,961,834 | A | 10/1999 | Hjerten | |
| 5,972,694 | A | 10/1999 | Mathus | |
| 6,068,775 | A | 5/2000 | Custer et al. | |
| 6,315,902 | B1 | 11/2001 | Collasius et al. | |
| 6,357,601 | B1 | 3/2002 | Bowers et al. | |
| 6,406,623 | B2 | 6/2002 | Petersen et al. | |
| 6,555,386 | B1 | 4/2003 | Rees | |
| 6,692,596 | B2 | 2/2004 | Moll et al. | |
| 6,692,702 | B1 | 2/2004 | Burshteyn et al. | |
| 6,692,968 | B2 | 2/2004 | Burshteyn et al. | |
| 6,759,233 | B2 | 7/2004 | Leonard | |
| 6,764,653 | B2 | 7/2004 | Zermani | |
| 6,818,184 | B2 | 11/2004 | Fullwyler et al. | |
| 7,108,791 | B2 * | 9/2006 | Tkacik et al. | 210/651 |
| 7,267,769 | B2 * | 9/2007 | Baird | 210/257.2 |
| 7,468,281 | B2 * | 12/2008 | Kallury et al. | 436/178 |
| 7,547,384 | B2 | 6/2009 | Keenan | |
| 2004/0132208 | A1 | 7/2004 | Burshteyn et al. | |
| 2004/0171169 | A1 | 9/2004 | Kallury et al. | |
| 2006/0121555 | A1 | 6/2006 | Lean et al. | |

OTHER PUBLICATIONS

Search Report and Written Opinion of the USPTO as ISA dated Sep. 27, 2007.

* cited by examiner

METHOD AND APPARATUS FOR THE FILTRATION OF BIOLOGICAL SAMPLES

RELATED APPLICATIONS

This is a continuation of application Ser. No. 11/615,031 filed Dec. 22, 2006 now U.S. Pat. No. 7,510,654, granted Mar. 31, 2009 and which claims the benefit of U.S. Provisional Application No. 60/755,009, filed Dec. 29, 2005, and U.S. Provisional Application No. 60/754,813, filed Dec. 29, 2005, which applications are hereby incorporated herein by reference in their entirety.

STATEMENTS REGARDING FEDERALLY SPONSORED RESEARCH

Not applicable

BACKGROUND OF THE INVENTION

1. Field of the Invention

The invention relates generally to a sample preparation membrane separation modules and methods and more specifically to single-pass tangential flow filtration operation for the concentration of liquid samples.

2. Description of the Related Art

Ultrafiltration (UF) and microfiltration (MF) membranes have become essential to the separation and purification in the manufacture and research of biomolecules. Biomolecular manufacturing and laboratory sample preparation, regardless of the scale, generally employs one or more processing steps including filtration (UF or MF). The attractiveness of these membrane separations rests on several features: including, for example, high separation power, and simplicity (e.g., requiring only the application of a pressure differential between feed and permeate). This simple and reliable one-stage "cut" of the sample into two fractions makes membrane separation processes a valuable approach to separation and purification.

In one class of membrane separations, the species of interest is that which is retained by the membrane, and the objective of the separation is typically to remove smaller contaminants, to concentrate the solution, or to affect a buffer exchange. In another class of membrane separations, the species of interest is that which permeates, and the objective is typically to remove larger contaminants. In MF, the retained species are typically particulates, organelles, bacteria or other microorganisms, while those that permeate are proteins, colloids, peptides, small molecules and ions. In UF the retained species are typically proteins and, in general, macromolecules, while those that permeate are peptides, ions and, in general, small molecules.

The ability to maintain a reasonably high flux is essential in the practice of membrane processes. Low flux can result in long filtration times or large modules, resulting in increased cost and large hold-up volumes (i.e., the volume including the retained species remaining in the module). The filtration process itself induces the creation of a highly concentrated layer of the retained species on the surface of the membrane, a phenomenon called "concentration polarization" (or simply "polarization"), which reduces the flux from an initial value obtained immediately at the start of filtration. In the absence of counter measures the accumulation of "polarized" particles or solutes results in vanishingly small fluxes and bringing the processes to a stand-still. One conventional approach to overcoming the effects of concentration polarization in the practice of ultrafiltration is to run the separation in "tangential flow filtration" (TFF) mode.

TFF modules are devices having flow channels formed by the membrane through which the feed stream flows tangentially to the surface of the membrane. The tangential flow induces a sweeping action that removes the retained species and prevents excessive accumulation, thereby maintaining a high and stable flux. Because higher tangential velocities produce higher fluxes, the conventional practice of TFF calls for the use of high velocities in the flow channels, which in turn result in very high feed rates. These high feed rates result in low conversion, typically less than 10% and often less than 5%. Low conversion means that the bulk of the feed stream exits the module as retentate without having been separated.

One commercially important area for UF separations and purification is at the preparation of analytical samples (e.g., sample volumes less than 100 ml). The application of conventional TFF processes to sample preparation at the analytical scale is generally believed not to be practical due to the complications inherent in the use of pumps and recirculation loops. As a result, UF separations at these scales are practiced almost exclusively in a "dead-ended" mode, resulting in an inherently low flux due to concentration polarization. Centrifugal UF devices have been developed for this scale to mitigate the low flux of dead-ended UF separations. However, while these have become the dominant format for analytical scale UF, they typically require centrifuges capable of exposing the UF device to accelerations as high as 14,000 g. Furthermore, in spite of these accelerations, many separations still require a long time, as high as one hour. Finally, the recovery of the retentate presents special difficulties in these approaches since it may be spread as a thin film over the surface of the membrane.

One prior art device disclosed in U.S. Pat. No. 4,761,230, Pacheco, et al., includes first and second housing sections with a flow channel extending therebetween. A membrane filter forms one boundary of the flow channel. A pair of reservoirs, one for feed and the other for permeate collection, are integrally formed with the first housing section. A fluid communication path is established from the first section to the second section and then through means of a deformable chamber to the flow channel. The deformable chamber is adjacent to a rigid surface that is integral with one of the housing sections and in this manner is adapted to pump fluid through the system when interfacing with a pump. This device also operates in a continuous recirculation mode during concentration of batch samples and includes a recirculation loop.

U.S. Pat. Nos. 6,692,702, Burshteyn, et al. and 6,692,968, Burshteyn, et al, teach a method for utilizing a filtration device for removing interferants from a sample containing cells in an automated apparatus is disclosed. The filtration device includes a microporous hollow fiber membrane having a plurality of pores sized to retain cells while allowing smaller diameter interferants to pass through the membrane. The apparatus also includes a means for moving the sample from a sample container to and from the filtration device. The disclosed method utilizes a vacuum source to aspirate the sample into a lumen of the hollow fiber membrane so that the sample is retained in the lumen space until expelled into an analysis container or transported to an analyzer.

None of the prior art devices and methods provides rapid, controlled conversion without the use of numerous venting valves, recirculation loops and pumps in addition to simple construction and operation. Thus, the need exists for devices and processes suited for sample preparation in life science and diagnostics laboratories which are able to yield high reliable flux and high conversion without the need of recirculation loops, numerous valves and intermediate pumps, and that can be readily driven by the low-pressure differentials and which are simple to control. It would also be desirable to operate a bio-processing separation at the sample preparation scale in a single-pass mode while providing a high conversion with a relatively low hold up volume and effective recovery of the separation products.

SUMMARY

It has been discovered that the use of separation modules suitable for sample-preparation having long thin channels with relatively large ratios of channel membrane area to channel void volume, to volume of a sample feed reservoir, and to volume of the feed sample, can yield relatively fast, high-conversion, low hold-up-volume, single-pass TFF (SPF) separations that can be driven with low pressures.

In accordance with one aspect of the present invention, a separation module for the filtration of a liquid sample includes a separation element having at least one flow channel with an inlet, an outlet and a surface including a ultrafiltration membrane. The module further includes a feed reservoir fluidly coupled to the channel inlet, a retentate reservoir fluidly coupled to the channel outlet, a permeate reservoir fluidly coupled to the separation element. The ratio of the membrane area of the separation element to the volume of the feed reservoir is greater than about 2 $cm^{-1}$. Such a module is capable of processing a sample in a single-pass mode while providing a high conversion with a relatively low hold up volume. The module yields high reliable flux and high conversion without the need of recirculation loops, numerous valves and intermediate pumps.

In accordance with a further aspect of the invention a separation module for the filtration of a liquid sample includes a separation element having at least one flow channel with an inlet, a surface comprising a filtration membrane; and a hydrophobic vent affixed to the channel distally from the inlet. The module further includes a feed reservoir fluidly coupled to the channel inlet; and a permeate reservoir fluidly coupled to the separation element. Such a module is capable of processing a sample in a single-pass mode without valves for venting and needs only a single low pressure source.

In accordance with still another aspect of the invention, a separation module for the filtration of a liquid sample includes a separation element having flow channel with an outlet and a surface comprising a filtration membrane. The module further includes a feed reservoir, a permeate reservoir fluidly coupled to the outlet and the flow channel is disposed within the feed reservoir. Such a module is capable of processing a sample in a single-pass mode using outside-in flow. In one embodiment, the specific membrane area of the module described below is greater than about 2 $cm^{-1}$.

In accordance with still another aspect of the invention, a separation module for the filtration of a liquid sample includes a hollow fiber having a thick wall forming a permeate reservoir and a thin lumen adapted to provide capillary motion of the liquid within the lumen. Such a module is capable of processing a very small sample in a single-pass mode using capillary forces as the permeation driving sources.

In accordance with another aspect of the invention a method for filtering a liquid sample includes the steps of supplying a predetermined volume of the liquid sample into a feed reservoir of a separation module, inducing the tangential flow of the liquid sample in the at least one flow channel by applying a first pressure differential between the feed reservoir and retentate reservoir, and inducing the permeation of a portion of the liquid sample through the filtration membrane into the permeate reservoir by applying a second pressure differential between one of the retentate reservoir and permeate reservoir and the feed reservoir and permeate reservoir. The separation module includes a separation element having at least one flow channel having an inlet, an outlet and surface comprising a filtration membrane. The separation module further includes the feed reservoir fluidly coupled to the channel inlet, a retentate reservoir fluidly coupled to the channel outlet, and a permeate reservoir fluidly coupled to the separation element, and has a ratio of the membrane surface area of the separation element to the volume of the feed reservoir which is greater than about 2 $cm^{-1}$. With such a technique, single-pass sample processing can be readily driven by low pressure differentials which are simple to control. In addition, independent control of TCP and TMP is possible and provides efficient use of the relatively large membrane area in the separation element to yield high controllable conversion by controlling residence time in the flow channel regardless of the length of the channel. Such a technique is useful in recovering the retentate fraction of a processed sample using a 3-volume device, having feed, retentate and permeate reservoirs.

In accordance with another aspect of the invention a method for filtering a liquid sample includes the steps of supplying a predetermined volume of the liquid sample into a feed reservoir of a separation module, inducing the permeation of a portion of the liquid sample through the filtration membrane into the permeate reservoir by applying a pressure differential between the feed reservoir and permeate reservoir, and inducing the flow of the liquid sample in the at least one flow channel by venting the flow channel. The separation module includes a separation element having at least one flow channel having an inlet and a surface comprising a filtration membrane. The separation module further includes the feed reservoir fluidly coupled to the channel inlet, and a permeate reservoir fluidly coupled to the separation element, a hydrophobic vent affixed to the channel distally from the inlet, and has a ratio of the membrane surface area of the separation element to the volume of the feed reservoir which is greater than about 2 $cm^{-1}$. With such a technique, single-pass sample processing can be readily driven by one low pressure differential without having to control valves to vent the flow channel. Such a technique is useful in recovering the permeate fraction of a processed sample using a 2-volume device, having feed and permeate reservoirs.

In accordance with another aspect of the invention a method for filtering a liquid sample in a sample reservoir includes the step of dipping a hollow fiber separation module into the sample reservoir. The module includes a separation element having a lumen with an ultrafiltration membrane and having an inlet, a flow channel coupled to the inlet, and a wall at least partially surrounding the channel. The method further includes the steps of drawing a predetermined volume of liquid sample into the lumen by capillary action by leaving the module inlet in the sample reservoir for a predetermined time, inducing the tangential flow of the liquid sample in the lumen by capillary action, and inducing, by capillary action, permeation of a portion of the liquid sample through the lumen membrane into a permeate reservoir formed by an inner and outer surface of the lumen wall.

Disclosed embodiments employing long thin flow channels and relatively high ratios of membrane area to channel void volume and feed reservoir volume, provide conversions, exceeding 50%, and low processing times, less than five minutes while allowing high retentate recovery or permeate recovery.

BRIEF DESCRIPTION OF THE DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings.

DETAILED DESCRIPTION OF THE INVENTION

Figure 1A:
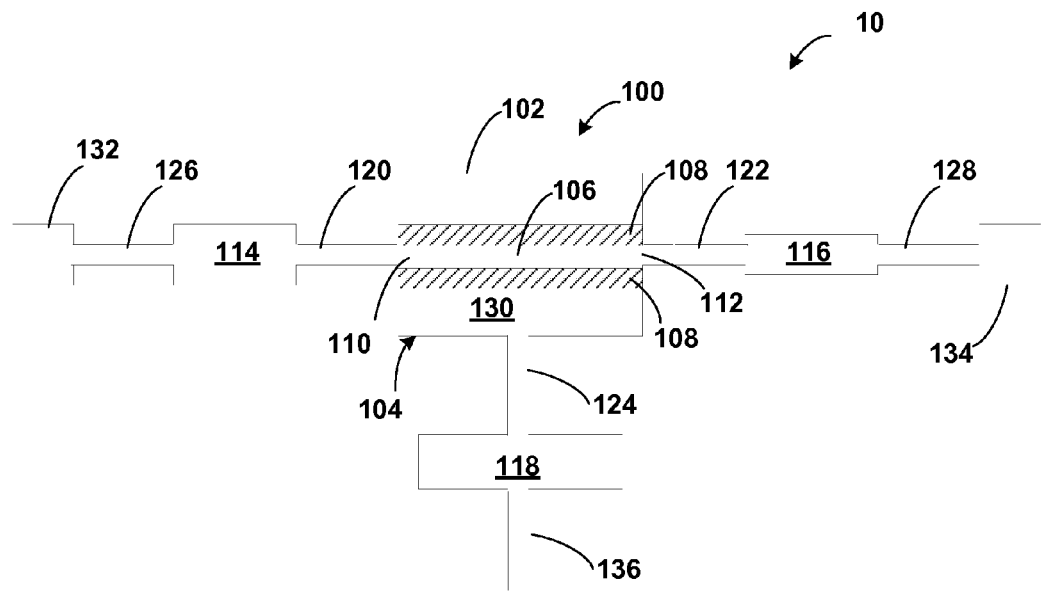
FIGS. 1A and 1B are schematic diagrams of 3-volume devices according to the invention.

It has been discovered that the use of separation modules suitable for sample-preparation having long thin channels with relatively large ratios of channel membrane area to channel void volume, volume of a sample feed reservoir, and volume of the feed sample, can yield relatively fast, high-conversion, low hold-up-volume, single-pass TFF (SPF) separations that can be driven with low pressures, compared to prior art devices. Some embodiments of the inventive module process feed samples in a single-pass through the module without the need of recirculation loops by applying pressure differentials between pairs of the feed reservoir, a permeate reservoir and a retentate reservoir. Other embodiments process the sample using a module having a feed reservoir and a permeate reservoir, in conjunction with a hydrophobic vent.

Prior to further describing the invention, it may be helpful to an understanding thereof to set forth definitions of certain terms to be used herein. The expressions "analytical scale sample preparation," "analytical sample preparation" and "sample-preparation" herein refers to applications where the sample volume is less than about 100 milliliters, in various embodiments, less than about 10 milliliter, and in still various embodiments, less than about 1 milliliter. The processes practiced in these applications are typically batch processes.

The terms "separation," "fractionation" and "purification" herein refer to the act of separating the feed sample into two streams, or fractions, permeate and retentate. The term "feed" and "feed stream" refer to the solution being fed to the filter for its separation. The term "permeate" refers to the fraction of the feed that has permeated through the membrane; the permeate is the stream depleted of at least a portion of the retained species. The term "retentate" refers to the fraction of the solution that has been retained by the membrane; the retentate is the stream enriched in the retained species. The term "conversion" is herein used to denote the fraction of the feed volume that permeates through the membrane in a single-pass through the flow channels, expressed in units of percentage of the feed stream volume. The term "recovery" will be used to denote the mass fraction of the species of interest recovered in the fraction of interest (permeate or retentate) expressed as a percentage of the mass contained in the feed sample.

The term "flux," symbol J, is herein used to describe the rate of permeation of the solution within the flow channel through the membrane, expressed herein with the units of liters per hour per $m^2$ of membrane area and abbreviated as "lmh." It is understood that the flux is identical to the liquid velocity perpendicular to the surface of the membrane at the surface of the membrane, and that it varies along the length of the channel, gradually decreasing along the flow direction of the channel from a high value at the proximal end (or feed end) of the channel to a low value at the distal end (or retentate end) of the channel. The expressions "specific membrane area of a flow channel," and "specific membrane area of the channel," are herein used synonymously to denote the amount of membrane area contained in the channel per unit channel void volume which can be expressed in units of $cm^{-1}$, and is given by the ratio:

$$\sigma_c = \frac{\text{Membrane Area of Flow Channel [cm}^2\text{]}}{\text{Void Volume of Flow Channel [cm}^3\text{]}} \text{ in units of [cm}^{-1}\text{]}. \quad (1)$$

As used herein, $\sigma_1$ represents the ratio of the membrane area of a separation element (i.e., the membrane area of the channels of the separation element) to the volume of the reservoir that includes the feed sample. This ratio is referred to as the specific membrane area of the module and is given by:

$$\sigma_1 = \frac{\text{Membrane Area of the Separation Element [cm}^2\text{]}}{\text{Volume of Feed Reservoir [cm}^3\text{]}} \text{ in units of [cm}^{-1}\text{]}. \quad (2)$$

It is understood that the reservoir including the feed sample is generally greater than or equal to the volume of the feed sample.

As used herein, $\sigma_M$ represents the ratio of the membrane surface area of separation element (i.e., the sum of the membrane area of the channels) to the volume of the feed sample itself. This ratio, the specific membrane area of the feed sample is defined by the following equation:

$$\sigma_M = \frac{\text{Membrane Area of the Separation Element [cm}^2\text{]}}{\text{Volume of Feed Sample [cm}^3\text{]}} \text{ in units of [cm}^{-1}\text{]}. \quad (3)$$

It will be appreciated that the processing time for a sample is related to the flux, the desired conversion, the volume of the feed reservoir, the volume of the sample, and the parameters $\sigma_M$ and $\sigma_1$.

The expressions "transmembrane pressure differential," "transmembrane pressure" and "TMP" are herein used synonymously to describe the average pressure differential between the flow channel, and the permeate compartment, and given by:

$$TMP = P_F - P_P; \quad (4)$$

where $P_F$=average of the pressure at the inlet and the outlet of the flow channel; and $P_P$=pressure at permeate compartment.

The expressions "transchannel pressure differential," "transchannel pressure" and "TCP" are herein used synonymously to describe the pressure differential between the feed port to the retentate port as follows:

$$TCP = P_{inlet} - P_R; \quad (5)$$

where $P_{inlet}$=pressure at the inlet of the flow channel; and $P_R$=pressure at retentate port. The pressure at the retentate port is essentially equivalent to the pressure at the outlet of the flow channel. For most 2-volume devices, described below, $P_R$ is the pressure at the end of the flow channel located distally from the inlet of the flow channel.

The term "dimensionless length" is herein used to describe the product of channel length, L, and the specific membrane area of a flow channel, $\sigma_c$, and is given by:

$$\lambda = \sigma_c L \quad (6)$$

The dimensionless length of a separation element having more than one channel is given by the sum of the dimensionless lengths of the channels in a serial flow path of the separation element. Additionally, some of the embodiments described herein utilize SPF modules having long channels, and more specifically, channels with high values of dimensionless parameter, $\alpha$, defined as follows:

$$\alpha = L\sqrt{\frac{\sigma_c^3}{\sigma_M}} \quad (7)$$

The term "ultrafiltration membranes" and "UF membranes" are used herein to refer to membranes that have pore sizes in the range between about one nanometer to about 100 nanometers. Such pore sizes, for example, can be useful for the separation of polymeric molecules from water and other low molecular weight solutes. Molecules that are too large to penetrate these pores are retained while water, dissolved salts and small molecules can pass through these pores. The retention behavior forms the basis for characterizing UF membranes, known as the "molecular weight cut off" of the membranes, and abbreviated as MWCO. In various embodiments, the present invention utilizes ultrafiltration membranes having MWCO ratings in the range from about 1,000 Daltons to several million Daltons.

The terms "hydrophobic vent" and "phobic vent" are used herein to refer to a microporous element that, by virtue of the hydrophobicity of its interior surface and the small pore size of its porous structure, allows the venting of gases while preventing the permeation of an aqueous liquid through its porous structure. Hydrophobic vents are known to those skilled in the art as elements useful for the reliable venting of gases without the need of valves and the intervention of an operator. Phobic vents are not generally used at pressures exceeding the intrusion pressure of the microporous structure, which for example is approximately 50 psi for elements having 0.2 µm pores.

As used herein the term "automatic" means performed without direct human intervention. For example, an automatic apparatus automatically performs a method when a component of the apparatus, rather than a human operator, performs one or more steps of the method, even though a human operator might input instructions into the machine or even perform one of the steps manually. Similarly, an "automated" method is a method performed automatically.

The inventive modules described herein can be provided in at least three configurations. In a first configuration, the module comprises three reservoirs, for accepting the feed sample volume, and for the recovery of the retentate and the permeate volumes, respectively; these are herein referred to as "3-volume" devices. In a second configuration, the module comprises two reservoirs, for accepting the feed sample volume, and for the recovery of the permeate volume, respectively; these are herein referred to as "2-volume" devices. In a third configuration, the module comprises a 2-volume configuration but with the flow channel in fluid communication with the permeate reservoir. In various embodiments, the present invention provides modules and methods for sample preparation of single samples. In various embodiments the present invention provides modules and methods for the substantially simultaneous sample-preparation of a large number of samples suitable for standard formats, as for example, multi-well plates and automated systems.

Ultrafiltration processes are used for concentration and diafiltration of solutions, occasionally as adjuncts to reaction processes. In various aspects of the present invention, the methods and modules can be used to concentrate the retained species. According to this concentration process, solvent is removed from the solution as well as any other solute that permeates through the membrane. The result is the concentration of those solutes that are retained by the membranes. Additionally, this concentration process purifies the retained species by the substantially simultaneous removal of those species that permeate through the membrane. In various aspects, the present invention provides methods and devices for single pass TFF (SPF) processing. In various embodiments, these methods and modules facilitate overcoming or even eliminating one or more of the drawbacks associated with conventional recirculation TFF approaches when attempted at the sample prep scale.

The present invention relates to the separation and purification of substances by membrane ultrafiltration, which is a pressure-driven separation process, and the driving forces to induce pressure differentials to effect the separation. SPF separations use two distinct pressure differentials: a first pressure differential to drive liquid flow tangentially along the surface of the membrane, the TCP, and a second pressure differential to drive the permeation across the membrane, the TMP. Suitable driving forces and sources to induce the necessary pressure differentials include, but are not limited to, centrifugal forces, compressed gases, vacuum sources, pumps, capillary forces, osmotic forces, electro-osmotic forces and combinations thereof.

For many laboratory applications pressure and vacuum sources are the most convenient. For example, a compressed gas (a pressure source) may be used to drive the feed solution, the same compressed gas at a lower pressure connected to the retentate reservoir can be used to control the TCP, while the permeate is kept at atmospheric pressure. A vacuum source may be used to drive the permeation by connecting a vacuum source, controlled at different vacuum levels, to the permeate and retentate reservoirs while the feed is kept at atmospheric pressure. In some cases it may be convenient to use both pressure and vacuum sources. There are a wide variety of vacuum and pressure sources well known to those skilled in the art. For example, a vacuum source can be a water driven aspirator or venturi, a central vacuum supply of the type commonly found in laboratories, a dedicated vacuum pump, or combinations thereof. A detailed list of means and devices for generating vacuums is given in Perry's Chemical Engineering Handbook, $6^{th}$ edition, McGraw-Hill, 1984, at pp. 6-32 to 6-37. Suitable pressure sources include, e.g., compressed gases from a cylinder with conventional means for regulating the applied pressure, using pressurized gas from a central source commonly available in laboratories, using a dedicated compressor from among the types described, for example, in Section 6 of Perry's Chemical Engineering Handbook, $6^{th}$ edition, McGraw-Hill, 1984, and combinations thereof.

Another driving force suitable for laboratory applications can be that based on osmotic forces. Osmotic forces induce pressure differentials by virtue of the difference in chemical composition of the solutions across the membranes. Another driving force suitable for laboratory applications can be that based on capillary forces. Capillary forces induce pressure differentials by virtue of the surface energy of the liquid within the flow channels and the membrane pores. The size of the driving force is inversely proportional to the size of the pores. Examples of embodiments that take advantage of capillary forces are discussed in more detail in conjunction with FIG. 16.

In the various aspects of the present invention, a channel comprises walls that are formed at least in part of an ultrafiltration membrane. While channels have a flow direction of liquid at any point of the channel, it should be understood that the channels need not be straight. Channels can be straight, coiled, arranged in zigzag fashion, and in general twist and turn in any spatial dimension. Channels can be open, for example, channels comprising hollow fiber membranes, or the channels can have flow obstructions, for example, rectangular channels formed by flat-sheet membranes spaced apart by woven or non-woven spacers.

Another driving force suitable for laboratory applications can be centrifugal acceleration, provided by placing the module in a suitable centrifugal field (e.g., in a laboratory centrifuge). In these embodiments, the spatial location of the various components of the module, feed reservoir, separation element, retentate reservoir and permeate reservoir, should be in a definite order for the centrifugal driving forces to effect the desired UF separation. It should be noted that in centrifugal devices the tangential driving force is controlled independently of the transmembrane driving force by the relative placement of the retentate and permeate reservoirs with respect to the feed reservoir. There are a wide variety of centrifuges suitable for applying a centrifugal acceleration for use in applying a driving force for the devices and methods of the present invention. Centrifuges include the "swinging bucket" or of the fixed bucket type, which are available for multi well plates as well as for single sample devices with acceleration levels of more than 1,000 g.

Referring to FIG. 1A, a sample preparation system 10 includes a 3-volume sample preparation module 100 comprising a housing 102, a separation element 104 disposed within the housing 102 comprising a permeate compartment 120 and at least one flow channel 106 having an inlet 110, an outlet 112 and a surface comprising a filtration membrane 108. The module 100 further comprises a feed reservoir 114 fluidly coupled to the channel inlet 110 through a feed flow passage 120, a retentate reservoir 116 fluidly coupled to the channel outlet 112 through a retentate flow passage 122, and a permeate reservoir 118 fluidly coupled to the separation element 104 through a permeate flow passage 124. The system 10 further includes a feed pressure source 132 and a retentate pressure source 134 coupled to the module 100. The module 100 additionally comprises a feed port 126 coupled to the feed reservoir 114 and coupled to the feed pressure source 132, a retentate port 128 coupled to the retentate reservoir 116 and coupled to the retentate pressure source 134, and a permeate port 136 coupled to the permeate reservoir 118.

In operation, the feed port 126 is used to introduce the feed sample into the feed reservoir 114 and then to connect the feed pressure source 132 to the feed reservoir 114. The retentate pressure source 134 is connected to the retentate reservoir 116, and the feed pressure is set to a higher pressure to provide positive pressure differentials between the feed port 126 and the permeate port 136 and between the feed port 126 and the retentate port 128. Here, the permeate reservoir 118 is vented to the atmosphere. The pressure differentials provide the necessary driving forces for tangential flow by inducing the TCP and for permeation by inducing the TMP. Timed application of these pressure differentials controls the conversion of the liquid sample volume in the feed reservoir 114 into the retentate volume in the retentate reservoir 116 and the permeate volume in the permeate reservoir 118. The pressure differentials are provided by combinations of pressure sources, vacuum sources, or by the application of centrifugal acceleration. In one embodiment, the pressures provided by the pressure sources 132 and 134 are lower than about 50 psi, in other embodiments lower than about 30 psi, and yet other embodiments lower than 15 psi.

Figure 1B:
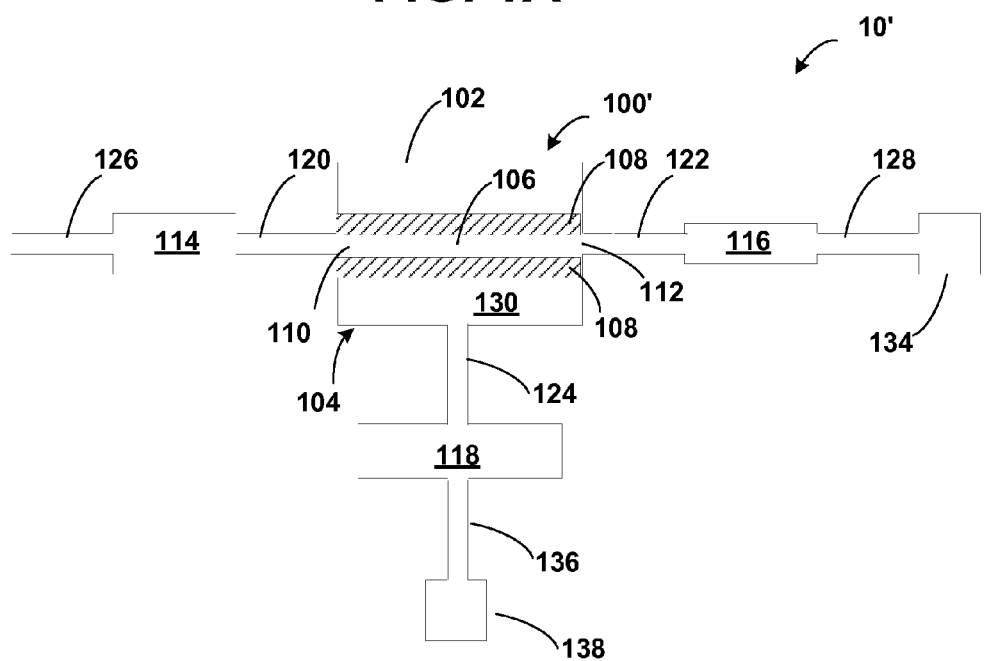

Now referring to FIG. 1B, in which like elements are provided having like reference designations as in FIG. 1A, a sample preparation system 10' includes a 3-volume sample preparation module 100' similar to module 100 of FIG. 1A and a pressure source 138 coupled to the permeate reservoir 118 via the permeate port 136. In addition, the feed reservoir 114 is vented to the atmosphere instead of being coupled to feed pressure source 132. In one embodiment, pressure sources 134 and 138 are vacuum pumps which provide positive pressure differentials between the feed port 126 and the permeate port 136 and between the feed port 126 and the retentate port 128. Here, pressure source 138 provides a stronger vacuum than pressure source 134. Table 1 lists some of the possible embodiments and pressure source combinations according to the invention, with configuration 1 corresponding to FIG. 1A and configuration 2 corresponding to FIG. 1B. In configurations 4 and 5 both the TMP and TCP are controlled without venting any of the volumes to the atmosphere. This is desirable if exposure of the liquids to oxygen or water vapor in the atmosphere is not desirable. If the liquid contains volatile components then the use of configuration 4 avoids possible vaporization.

In one embodiment, the specific membrane area of the module, $\sigma_1$, is greater than about 2 $cm^{-1}$ and in other embodiments greater than about 5 $cm^{-1}$, and still another embodiment greater than about 10 $cm^{-1}$. The channels in some of these embodiments have specific membrane area of the channel, $\sigma_c$, greater than about 40 $cm^{-1}$, some greater than about 80 $cm^{-1}$, and other embodiments greater than about 130 $cm^{-1}$ depending on the feed stream and the membrane used for the separation. Generally the ratio of $\sigma_c$ to $\sigma_1$ is greater than about 1, greater than about 3, and often greater than about 10. This ratio affects the fraction of retentate left in channel and therefore the hold up volume. These embodiments generally have a dimensionless parameter $\alpha$ greater than about 10,000. In one embodiment modules 100 and 100' are used with sample volumes and have membrane areas such that the specific membrane area of the feed sample, $\sigma_M$, is greater than about 2 $cm^{-1}$, in other embodiments greater than about 5 $cm^{-1}$, and in still other embodiments greater than about 10 $cm^{-1}$. In these embodiments the ratio of $\sigma_M$ to $\sigma_1$ is generally greater than about 1, greater than about 3, and often greater than about 10.

TABLE 1

MODULE PRESSURE SOURCES

| Configuration | Feed | Permeate | Retentate | Pressure Sources |
|---|---|---|---|---|
| 1 Vented Permeate | Pressure1 | Atmosphere | Pressure2 | P1 > P2 |
| 2 Vented Feed | Atmosphere | Vacuum1 | Vacuum2 | V2 < V1 |
| 3 Vented Retentate | Pressure | Vacuum | Atmosphere | |
| 4 Un-vented A | Pressure1 | Pressure2 | Pressure3 | P1 > P3 > P2 |
| 5 Un-vented B | Vacuum1 | Vacuum2 | Vacuum3 | V2 > V3 < V1 |
| 6 Sealed Retentate A | Pressure | Atmosphere | Sealed | |
| 7 Sealed Retentate B | Atmosphere | Vacuum | Sealed | |
| 8 Centrifugal Force | Atmosphere | Atmosphere | Atmosphere | |

Figure 2:
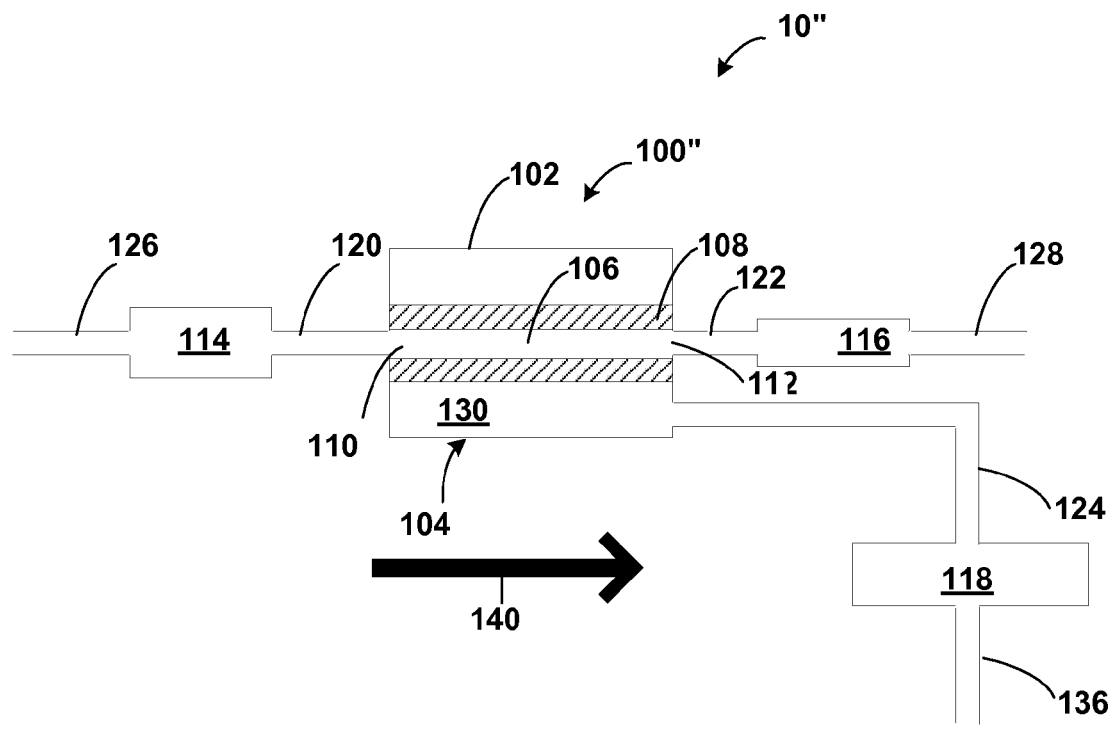
FIG. 2 is a schematic diagram of a 3-volume device similar to the devices of FIG. 1A suitable for operation in a centrifuge.

Now referring to FIG. 2, in which like elements are provided having like reference designations as in FIG. 1A, a sample preparation system 10" includes a 3-volume sample preparation module 100" similar to module 100 of FIG. 1A. Here, the system 10" does not include any directly coupled pressure sources. The feed reservoir 114, retentate reservoir 116 and permeate reservoir 118 are vented to the atmosphere instead of being coupled to pressure sources. Here the driving forces are provided by a centrifuge (not shown) with a centrifugal acceleration vector indicated by arrow 140. The feed reservoir 114, the retentate reservoir 116 and the permeate reservoir 118 are juxtaposed along the centrifugal acceleration vector 140, the retentate reservoir 116 interposed between the feed reservoir 114 and the permeate reservoir 118. In one embodiment as shown in FIG. 2, the retentate reservoir 116 and the permeate reservoir 118 can overlap on an axis perpendicular to the centrifugal acceleration vector 140. The embodiment of FIG. 2 corresponds to configuration 8 in Table 1.

In operation, the centrifuge provides the pressure differential driving forces. The location and orientation of the three reservoirs 114, 116 and 118 and the separation element 100" with respect to the centrifugal acceleration vector 140 determine the TCP and TMP. In various embodiments, the relative location of the separation element 100" and the retentate reservoir 116 provides the ability to control induced TCP substantially independently of the induced TMP. The local pressure in system 10" is set by the liquid position relative to the location of the liquid level in the feed reservoir multiplied by the centrifugal acceleration vector. Hence the placement of the retentate reservoir 116 closer to the feed reservoir 114 insures the TCP is controlled independently of the TMP, which is set by the distance between the liquid level in the feed reservoir 114 and the liquid level in the permeate reservoir 118 along centrifugal acceleration vector.

The ports 126, 128 and 136, and flow passages 120, 122 and 124 are depicted to illustrate one embodiment for adding and removing liquids as well as venting to the atmosphere and are not intended to limit the invention in any way. Depending on the application, vacuum and other pressure sources are optionally connected to the ports 126, 128 and 136 to induce the pressure differentials necessary to drive the process.

Separation elements are preferably composite structures comprising flow channels for directing the feed, retentate and permeate as well as other elements to support the separation process. The present invention utilizes separation elements made with ultrafiltration membranes. Ultrafiltration membrane structures can be described by three broad structural categories: tubular, sheet and monolithic. Hollow fiber membranes are a kind of tubular UF membrane, with an inner diameter of typically between 0.1 and 1.0 millimeters whose inner surface is the separating membrane. In various applications, the feed solution to be processed flows through the inside of the hollow fiber membrane, hereafter referred to as the "lumen," and the permeate leaves on the outside of the fibers.

Sheet membranes can be made in various forms and typically are laminated to some sort of cloth support. Two sheets of membrane separated by a highly permeable net-like structure, or spacer, forms the flow channel. A wide variety of sheet membranes can be used in various embodiments of the present invention, including, but not limited, non-planar sheets and monolithic membranes. For example, membranes with undulating, dimpled or corrugated surfaces are examples of non-planar sheet membranes.

Figure 3:
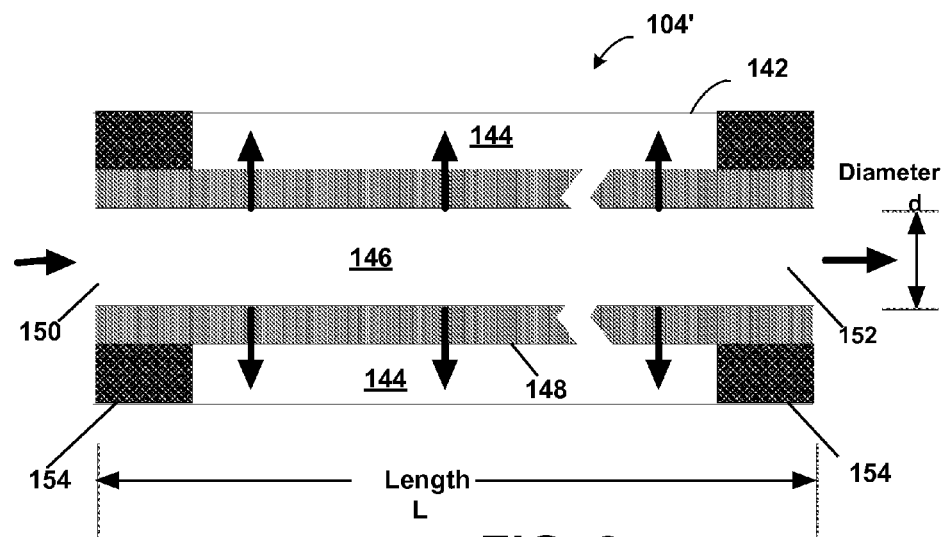
FIG. 3 is a longitudinal cross section view of flow a channel formed with hollow fiber membrane according to the present invention.
Figure 4:
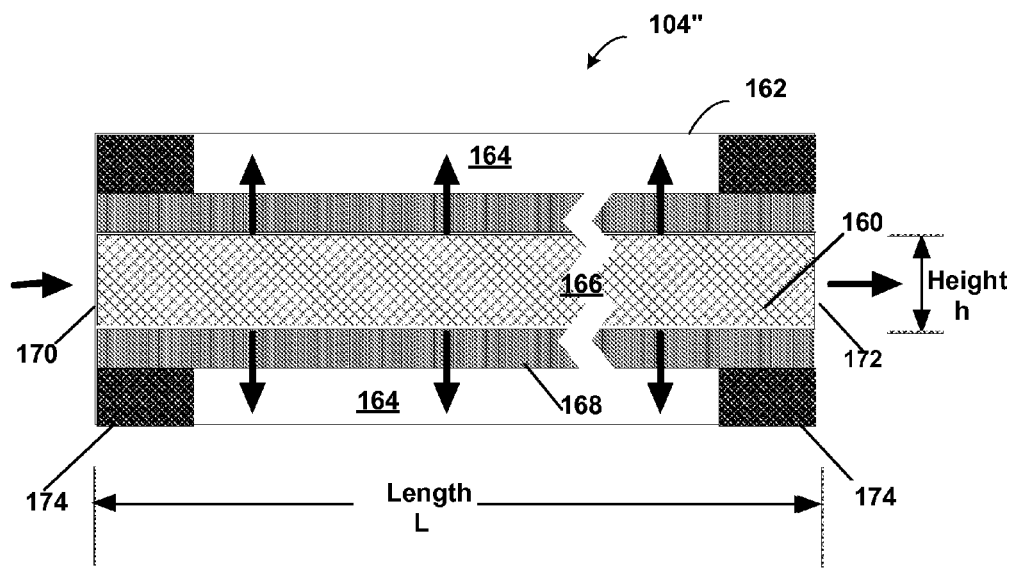
FIG. 4 is a longitudinal cross section view of a flow channel formed with flat-sheet membranes according to the present invention.

In various aspects, the modules of the present invention include separation elements made of conventional ultrafiltration membranes in any of the multiple topologies available. FIG. 3 schematically depicts a flow channel using hollow fiber membranes, while FIG. 4 schematically depicts a flow channel using flat-sheet membranes.

Now referring to FIG. 3, an exemplary hollow fiber separation element 104' similar to the separation element 104 of FIG. 1A includes a housing 142 and a hollow fiber ultrafiltration membrane 148 disposed within the housing 142. The membrane 148 forms a flow channel 146. The module 104' further includes seals 154 disposed adjacent a channel inlet 150 and a channel outlet 152 to separate the feed stream in the channel 146 from the permeate compartment 144. In operation, the feed enters the flow channel 146 at the channel inlet 150, flowing tangentially over the membrane 148 towards the channel outlet 152, driven by, for example, a transchannel pressure differential, TCP, and a transmembrane pressure differential, TMP, generated by at least one pressure source (not shown). As a result of the TMP a portion of the feed permeates through the membrane 148 as indicated by flow arrows providing the permeate in the permeate compartment 144. The flow channel 146 formed by the hollow fiber membrane 148 can be further described by its length, L, and lumen diameter, d, as shown in FIG. 3. Flow channels formed with hollow fiber membranes are typically open with no flow obstructions. The specific membrane area, $\sigma_c$, of the flow channel 146 is defined as the ratio of the membrane area contained in the channels divided by the void volume of the channel 146. For channels formed with hollow fiber membranes the specific membrane area of the flow channel is derived from equation 1 as:

$$\sigma_C = \frac{4}{d}. \tag{8}$$

In one embodiment, the flow channel 146 has a specific membrane area greater than about 50 $cm^{-1}$, and in this embodiment the membrane has a hydraulic permeability greater than about 2 lmh/psi. In another embodiment the specific membrane area is greater than about 80 $cm^{-1}$, and in yet another embodiment the specific membrane area is at least about 130 $cm^{-1}$. High specific membrane areas result in higher flux and reduced hold-up-volume of the SPF module. For hollow fiber channels the dimensionless length is given by:

$$\lambda = 4\frac{L}{d}. \tag{9}$$

In one embodiment the dimensionless length, $\lambda$, of the flow channel of a module comprising hollow fiber flow channels is greater than about 2,000, in another embodiment greater than about 4,000 and in yet another embodiment greater than 10,000. The values of specific membrane area, $\sigma_c$, and dimensionless length, $\lambda$, in these embodiments enable the hollow fiber module 104' to function effectively in a SPF sample preparation process similar to the process described below in conjunction with FIG. 8. In one embodiment the ratio of the membrane area of the separation element to the volume of the feed reservoir, $\sigma_1$, is greater than about 2 $cm^{-1}$.

Referring to FIG. 4, an exemplary flat-sheet separation element 104" similar to the separation element 104 of FIG. 1A includes a housing 162 and a flat-sheet ultrafiltration membrane 168 disposed within the housing 162. The membrane 168 forms a flow channel 166 supported by a spacer 160 interposed between two surfaces of the membrane 168. The module 104' further includes seals 154 disposed adjacent a channel inlet 150 and a channel outlet 152, to separate the feed stream in the channel 146 from the permeate compartment 144. In one embodiment, channel 166 is formed by sandwiching the spacer 160 between two sheets of flat-sheet membrane 168. Channel 166 formed in this manner is referred to as a rectangular channel since it possesses a rectangular cross-section, although it is to be understood that SPF channels are not limited to rectangular cross-sections or any specific topology.

In operation, the feed stream enters the flow channel 166 at the channel inlet 170, flowing tangentially over the membrane 168 towards the channel outlet 172, driven by, for example, a transchannel pressure differential, TCP, and a transmembrane pressure differential, TMP, generated by at least one pressure source (not shown). As a result of the TMP a portion of the feed permeates through the membrane 168 as indicated by flow arrows providing the permeate in the permeate compartment 164. The flow channel 166 formed by the flat sheet membrane 168 is further described by its length, L, and height, h, as shown in FIG. 4. The feed stream can be distributed across the width of the channel 166 by appropriate feed distributors (not shown). The retentate can be collected along the width of the channel 166 by appropriate retentate distributors (not shown). The spacer 160 maintains the membranes in a spaced apart arrangement, and edge seals 174 enclose the channel 166 and form a portion of the permeate compartment 164. There are numerous techniques for forming edge seals known to those skilled in the art. The spacer 160 can be a woven, non-woven, or molded structure, or combinations thereof, that allow the percolation of liquid between its solid structures but are also sufficiently rigid to maintain the channel height h when exposed to compressive loads. The "void fraction" of the spacer 160, $\epsilon$, defined as the ratio of the void volume contained within the spacer to the total volume occupied by the spacer 160, and the structure of the spacer 160 affects the void volume as well as the hydraulic resistance of the channel 166. In one embodiment the spacer 160 is a turbulence-promoting spacer.

The calculation of the specific membrane area, $\sigma_c$, and the dimensionless length $\lambda$, can be provided for a specific channel topology using the channel height h, and void fraction, $\epsilon$. For example, for rectangular channels, the specific membrane area of the channel is derived from equation 1 as follows:

$$\sigma_C = \frac{2}{\epsilon h}; \tag{10}$$

where:
h is the height of the channel; and
$\epsilon$ is the void fraction of the spacer.
The dimensionless length, $\lambda$, is derived from equation 5 as follows:

$$\lambda = 2\frac{L}{\epsilon h}; \tag{11}$$

where:
L is the length of the channel;
h is the height of the channel; and
$\epsilon$ is the void fraction of the spacer.
Specific formulas for these parameters for channels having alternative topologies can be derived from the dimensions of the channel 166 or can be computed empirically as is known in the art. In one embodiment, the channel 166 has a specific membrane area greater than about 40 cm$^{-1}$ and in another embodiment the channel 166 has a specific membrane area greater than about 80 cm$^{-1}$.

Figure 5A:
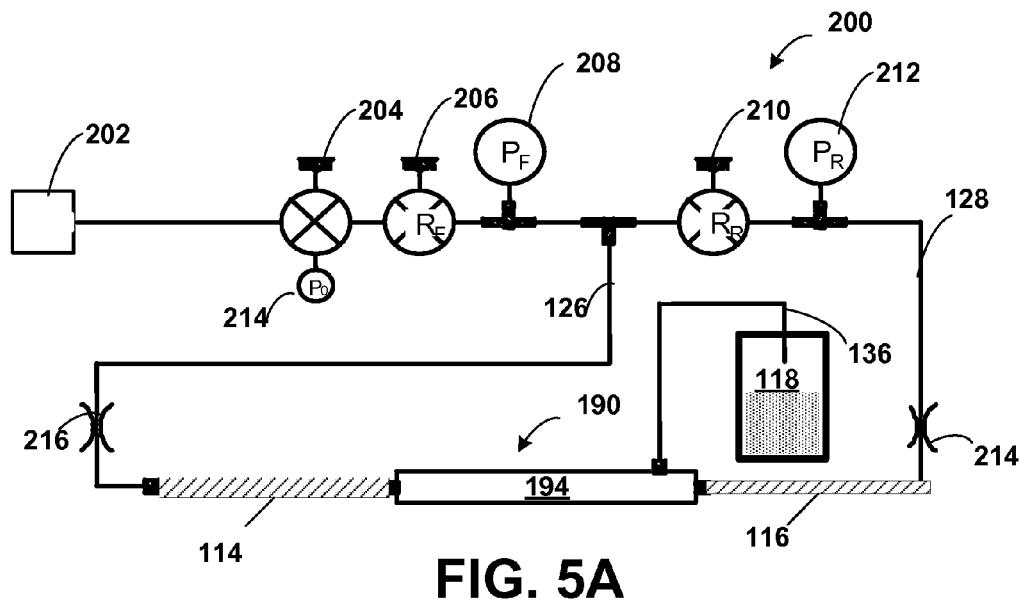
FIGS. 5A and 5B are schematic diagrams of instrumented systems incorporating the devices of FIGS. 1A and 1B.

Now referring to FIG. 5A, in which like elements are provided having like reference designations as in FIG. 1A, an instrumented sample preparation system 230 includes a 3-volume sample preparation module 190 similar to module 100 of FIG. 1A. System 230 further includes a pressure source 202, here, a source of compressed nitrogen gas N$_2$, a pressure regulator 204 coupled to the pressure source 202, coupled to feed and retentate pressure regulators 206 and 210. The feed pressure regulator 206 is coupled to a precision pressure gauge 208, and 206, and retentate pressure regulator 206 is coupled to a precision pressure gauge 212. In one embodiment, feed and retentate reservoirs 114 and 116 comprised ⅛" and ¹⁄₁₆" ID clear Tygon tubing, respectively. The system 200 also includes valve 216 (e.g., a pinch valve) installed on feed port 126 and valve 214 (e.g., a pinch valve) installed on retentate port 128. The various embodiments of separation element 194 are described below in conjunction with Examples 1-5.

In operation, the main system pressure is regulated with pressure regulator 204 and the feed and retentate pressures are precisely controlled by means of the precision pressure regulators 206 and 210, here for example, 0-30 psi, 20-turn pressure regulators, and monitored by pressure gauges 208 and 212, here 0-30 psi, digital gauges with 0.01 psi resolution. Initially the permeate reservoir 118, here directed to a waste container (not shown) is maintained at atmospheric pressure, therefore the inlet TMP is equal to the feed pressure measured at gauge 205, and the TCP is controlled to the desired value by means of pressure regulator 210 where TCP=$P_F$–$P_R$. The progress of the ultrafiltration sample processing is monitored by measuring the length of the liquid column in the reservoirs, the feed reservoir 114 containing approximately 80 microliters per centimeter of length and the retentate reservoir 116 containing approximately 20 microliters per centimeter of length. It is understood that some or all of these operations can be performed manually or the steps could be automated. An automated embodiment (not shown) includes but is not limited to a programmable controller to control pressure differentials and timing, volume sensors, flow sensors, and concentration sensors.

Figure 5B:
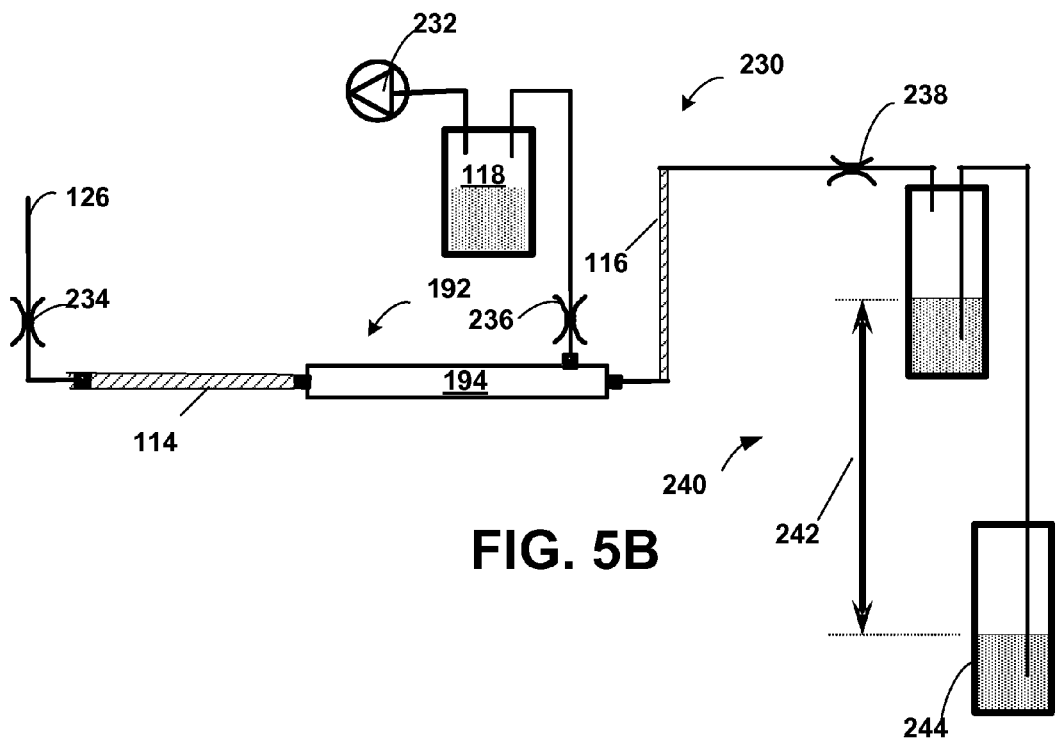

Now referring to FIG. 5B, in which like elements are provided having like reference designations as in FIG. 1B, an instrumented sample preparation system 230 includes a 3-volume sample preparation module 192 similar to module 100' of FIG. 1B. System 230 includes a vacuum source 232 as a first pressure source, here, a vacuum pump was capable of generating vacuums exceeding 29 in-Hg. Since no attempt was made to regulate the vacuum, (i.e., the vacuum pump was connected directly to permeate pinch valve 236), the vacuum can be considered to be a full vacuum. System 230 further includes a gravity siphon 240 as a second pressure source. The operation of system 230 is described below in conjunction with Examples 3 and 4.

Figure 6A:
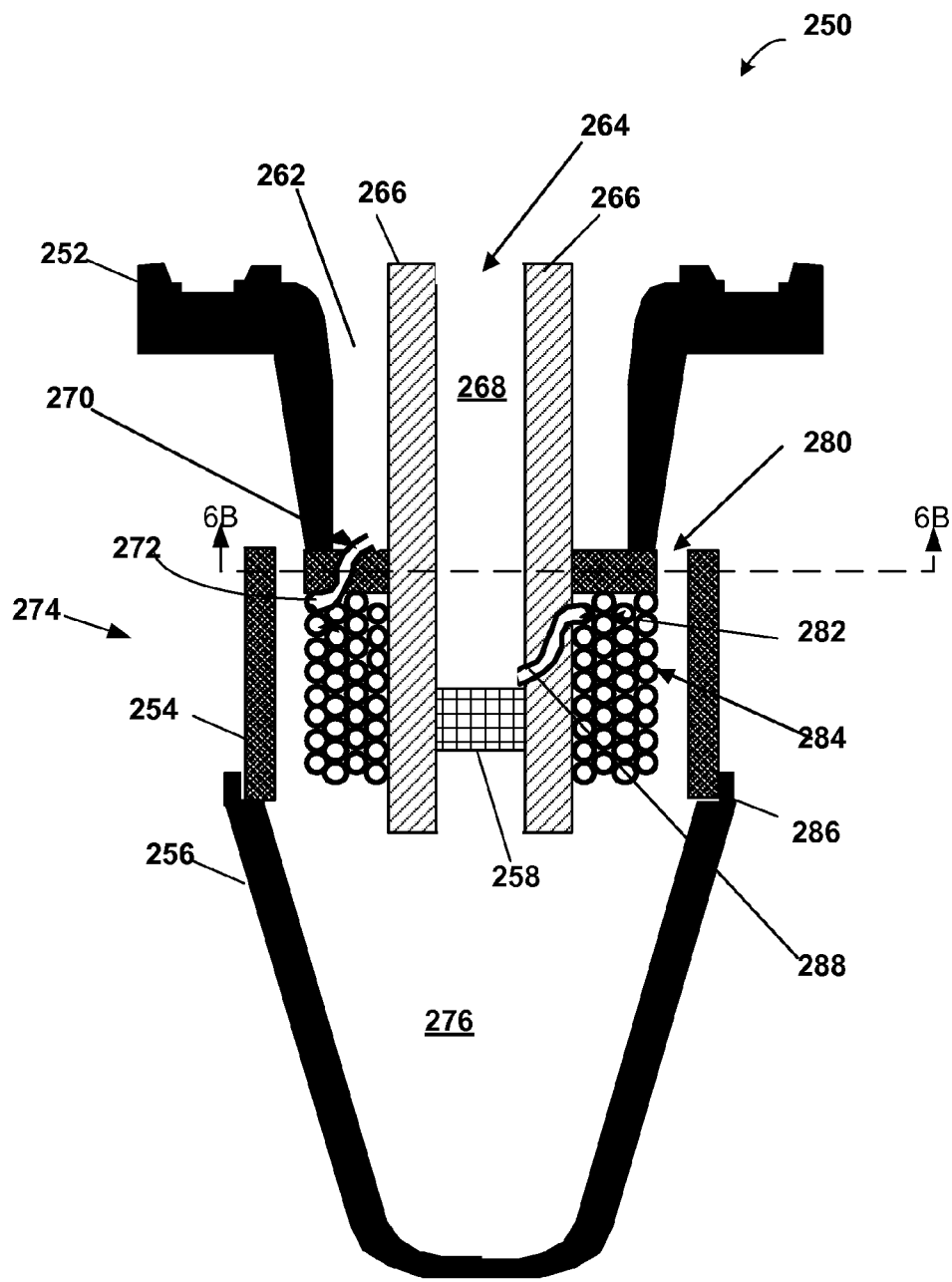
FIG. 6A is a cross-sectional view of a 3-volume device including a separation element comprising a hollow fiber membrane and suitable for use in multi-well plates according to the present invention.

Referring to FIG. 6A, a 3-volume module 250 comprises a housing 252, a hollow central core 266 having a plug 258 and forming a retentate reservoir 268, disposed within the housing 252. The housing 252 including a housing wall 254 and a portion of the central core 266 form a feed reservoir 262. The module 250 further comprises a permeate reservoir 276, a retentate port 264 for connecting a pressure source (not shown) to the retentate reservoir 268 and a permeate port 280 for connecting a pressure source (not shown) to the permeate reservoir 276. The module 250 further comprises a separation element 274 surrounding a portion of the central core 266.

The separation element 274 comprises a flow channel 284 comprising a hollow fiber membrane, a flow passage 270 fluidly coupling the feed reservoir 262 to a proximal end 272 of the flow channel 284. A distal end 282 of the flow channel 284 is fluidly coupled to the retentate reservoir 268 by a flow passage 288. In one embodiment, the permeate reservoir 276 is located below the separation element 274, thereby receiving the permeate by virtue of gravity. In this embodiment, the permeate reservoir 276 is optionally detachable from the housing 252 by means of a mating flange 286 coupled to the housing wall 254 to enable the transport of the permeate separately from the rest of the module.

In operation, the feed sample in introduced into the feed reservoir 262, a first vacuum source (not shown) is connected via port 264 to the retentate reservoir 268, while a second vacuum source (not shown) is connected via port 280 to the permeate reservoir 276, the second vacuum source providing a more negative pressure that the first vacuum source. The separation element 274 comprises in one embodiment a single hollow fiber in wound around the central core 266. In one embodiment, the hollow fiber has a lumen diameter of about 200 micrometers, resulting in a value of $\sigma_C$ of about 200 cm$^{-1}$. The separation element 274 in this embodiment has a surface area of about 3 square centimeters and the volume of feed reservoir 262 is about 100 microliters, resulting in a value of $\sigma_1$ of about 30 cm$^{-1}$. It will be appreciated that more that one flow channel 284 could be included in separation element 274 and that the flow channels could be coupled serially to provide additional membrane surface area.

Although embodiments utilizing vacuum sources are described, it is to be understood that embodiments utilizing pressure sources are also possible. In various embodiments, the permeate reservoir is at atmospheric pressure and the first and second pressure sources are connected to the feed and retentate reservoirs, respectively. This configuration advantageously provides a long thin channel (e.g., λ greater than about 2,000) in a compact device. An array of modules 250 can also be used in an automated sample processing system (e.g., a multi-well plate device) using sample handling techniques known in the art.

Figure 6B:
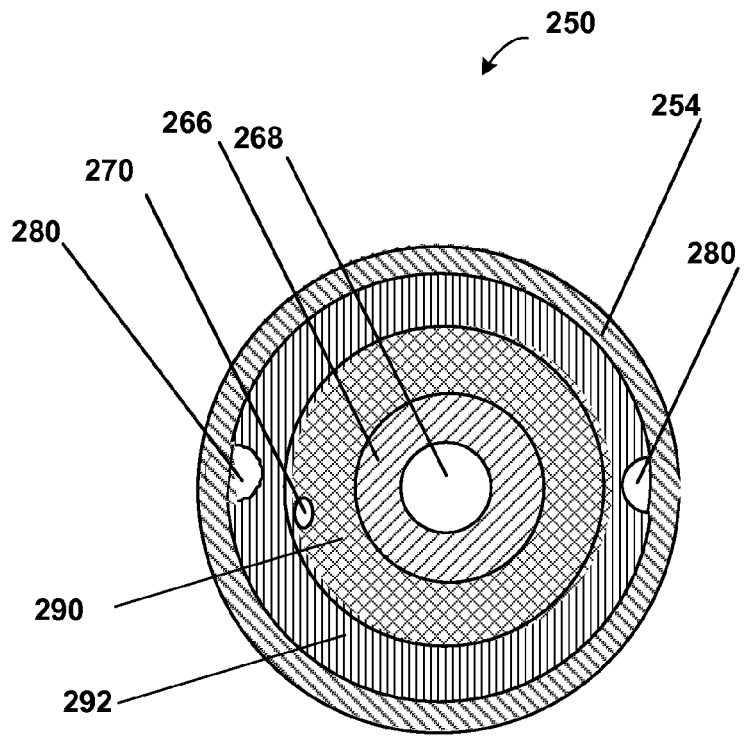
FIG. 6B is a cross-sectional view of the device of FIG. 6A, through line 6B of FIG. 6A, showing further details of the separation element.

Now referring to FIG. 6B, in which like elements are provided having like reference designations as in FIG. 6A the module 250 further comprises a support ring 290 connecting to the central core 266 and a support seal 292 which connects to the housing wall 254. The permeate port 280 passes through the support seal 292 which is connected to the support ring 290 and the housing wall 254. The flow passage 270 fluidly coupling the feed reservoir 262 to the proximal end 272 of the flow channel 284 passes through the support ring 290.

Figure 7B:
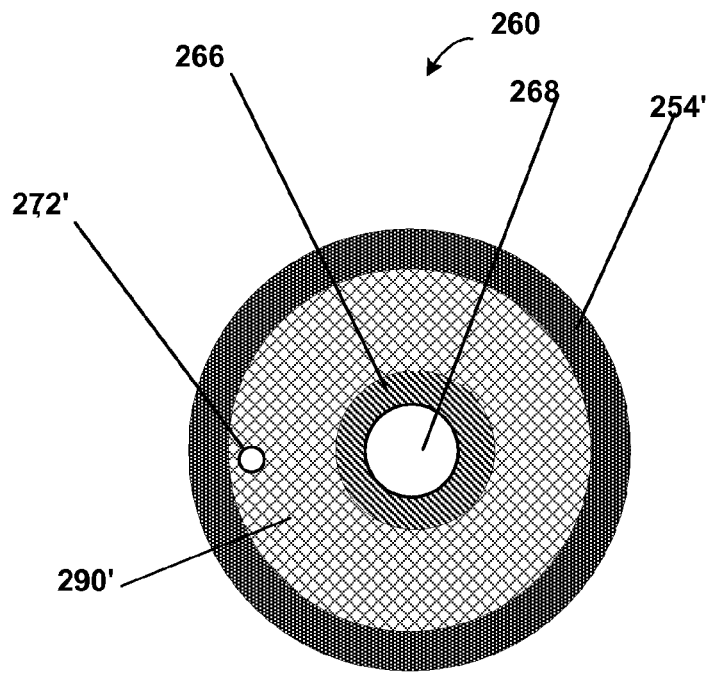
FIG. 7B is a cross-sectional view of the device of FIG. 7A, through line 7B of FIG. 7A, showing further details of the separation element.
Figure 7A:
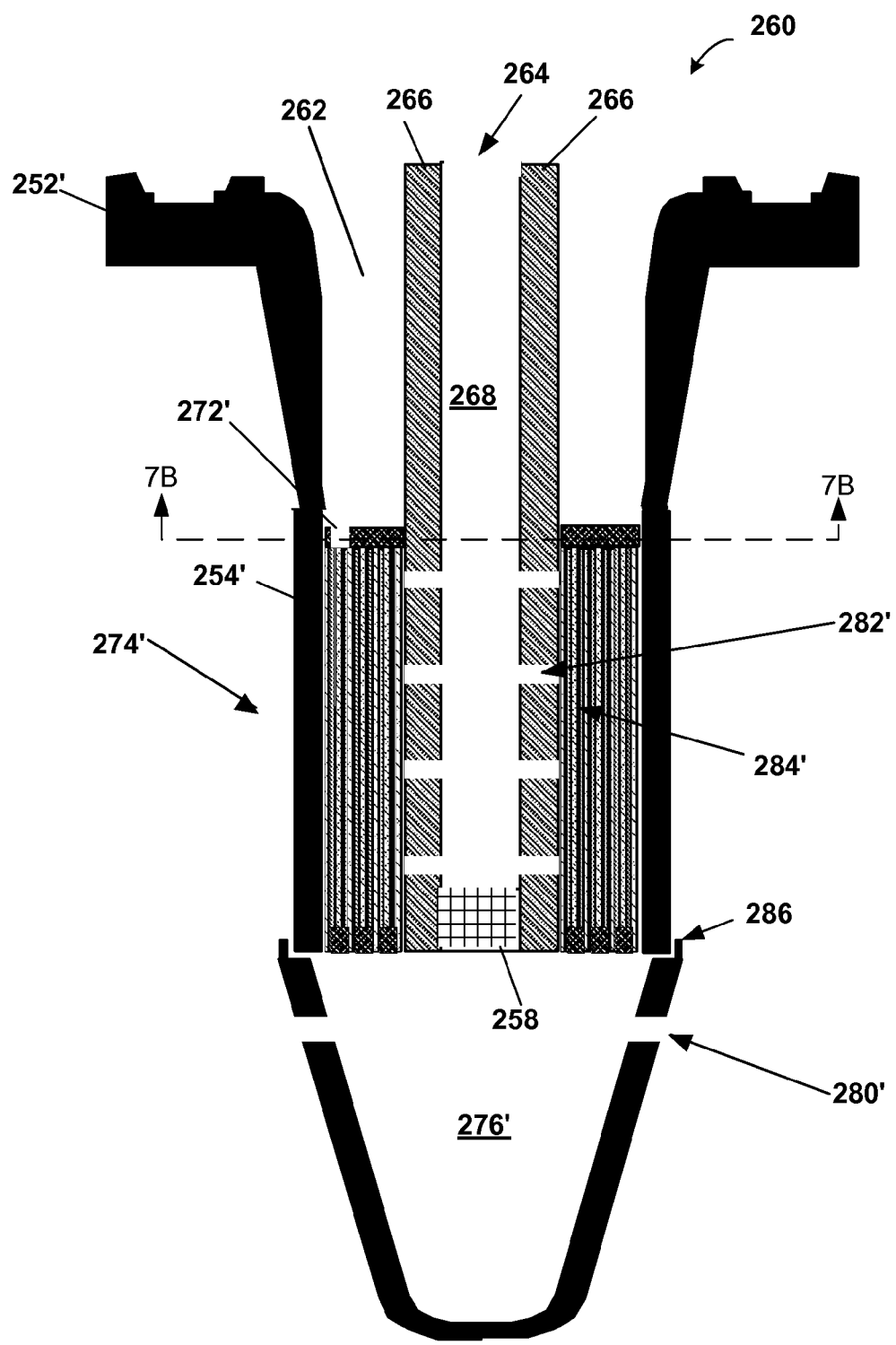
FIG. 7A is a cross-sectional view of a 3-volume device including a separation element comprising spiral-wound membrane and suitable for use in multi-well plates according to the present invention.

Now referring to FIG. 7A, in which like elements are provided having like reference designations as in FIG. 6A, a 3-volume module 260 similar to module 250, comprises a separation element 274' comprising a flow channel 284' comprising a flat-sheet membrane in a spiral-wound configuration instead of the hollow fiber membrane of separation element 274. Module 260 includes permeate ports 280' coupled directly to a permeate reservoir 276' for connecting a pressure source (not shown) to the permeate reservoir 276'. The spiral-wound separation element 274' comprises a single leaf comprising a rectangular channel formed with spacers having a channel height of about 100 micrometers and a porosity of about 0.7, resulting in a value of $\sigma_C$ of about 285 cm$^{-1}$. In one embodiment, the separation element 274' has a surface area of about 4.5 square centimeters and the volume of feed reservoir 262 is about 100 microliters, resulting in a value of $\sigma_1$ of about 45 cm$^{-1}$.

In operation, the feed enters the proximal end of flow channel 284' through flow passage 272'. The flow spirals inwardly until it reaches the distal end of the flow channel 284', at which point it enters the retentate reservoir 268 through flow passages 282'. In one embodiment, the permeate reservoir 276' is at atmospheric pressure and first and second negative pressure sources (e.g., vacuum sources) are coupled to the feed reservoir 262 and retentate reservoir 268, respectively. While FIG. 7A represents an embodiment driven by vacuum sources, it is understood that embodiments utilizing positive pressure sources are also possible.

It is understood that the sample processing using modules 250 and 260 driven by positive pressure or negative pressures can utilize pumps to provide positive pressure and vacuums to provide negative pressures. For example, a peristaltic pump, automated pneumatic and electric or manually operated syringe pumps may be advantageously used to generate both pressures. In certain embodiments, the feed and retentate displacement volumes determine the conversion. To operate modules 250 and 260 in such a "fixed conversion" mode, the feed sample is loaded into a large syringe pump (not shown) coupled to the proximal end of flow channels 284 and 284', respectively, and a smaller syringe pump (not shown) is fluidly coupled to the distal end of flow channels 284 and 284', respectively. In this manner, the displacement volumes of the large and small syringe pumps can become the feed and retentate volumes, respectively, integrated into modules 250 and 260 to induce the pressure differentials.

Now referring to FIG. 7B, in which like elements are provided having like reference designations as in FIG. 7A the module 260 further comprises a support ring 290' connecting the housing wall 254' to the central core 266. The flow passage passes through the support ring 290' which provides a seal at the end of the spiral wound separation element 274'. In addition, the permeate ports 280' are coupled directly to a permeate reservoir 276' by a support seal (not shown).

Figure 8:
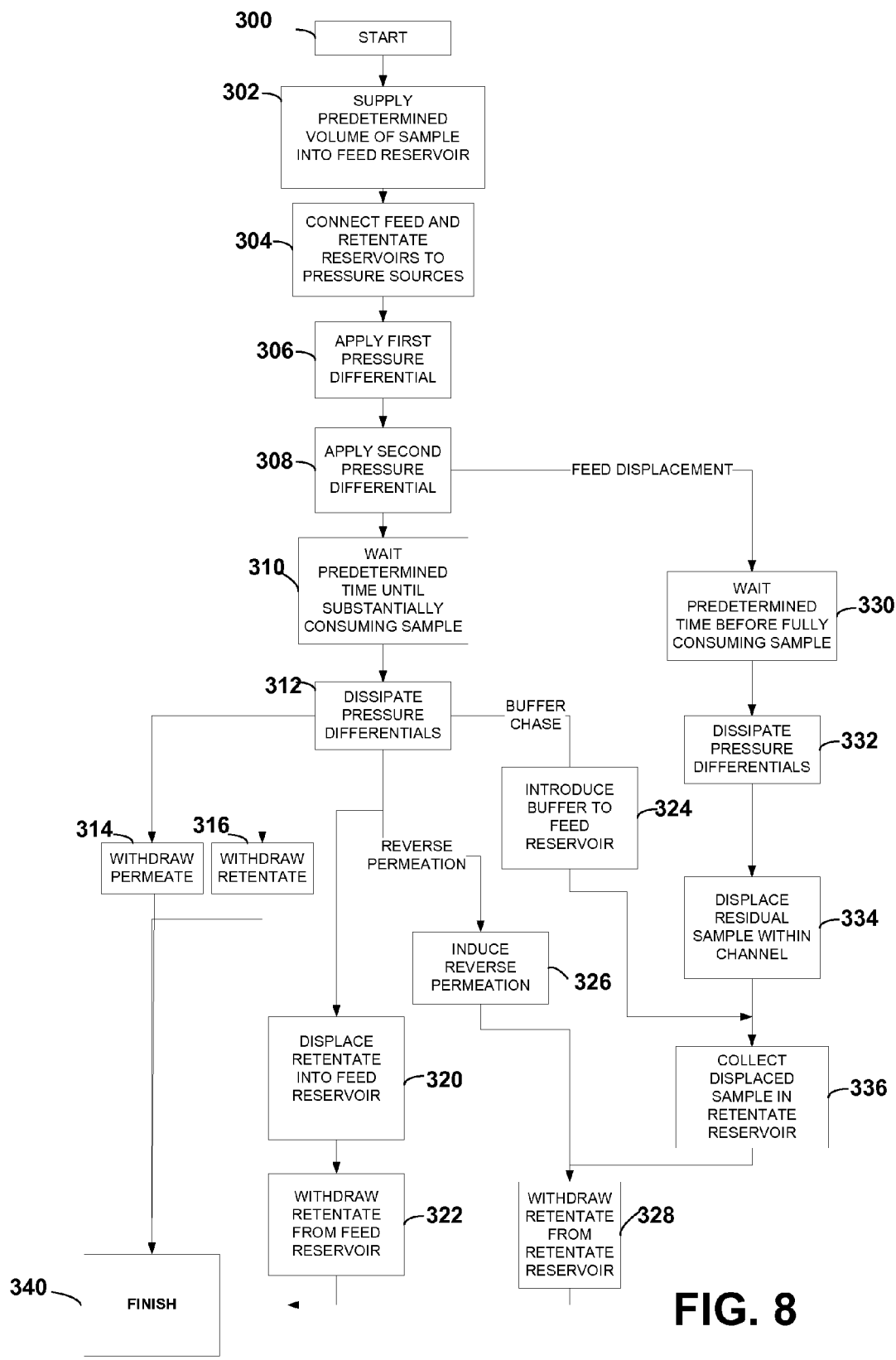
FIG. 8 is a flow diagram illustrating the steps used to process a sample and recover the retentate or permeate fractions using the devices of FIGS. 1A, 1B, and 2.

Turning now to FIG. 8, a flow diagram illustrates a process for processing a sample and recovering either the retentate fraction or the permeate fraction using 3-Volume devices. In the flow diagrams of FIGS. 8 and 15, the rectangular elements are herein denoted "processing blocks" (typified by element 302 in FIG. 8) and represent manual processing steps. Alternatively, the processing blocks represent steps performed by functionally equivalent automated equipment. It will be appreciated by those of ordinary skill in the art that some of the steps described in the flow diagrams may be implemented automatically while others may be implemented in a different manner (e.g. via a manual procedure) and that both positive pressure source and negative pressure (e.g., vacuum) sources can be used in SPF sample processing, both positive and negative pressure sources collectively referred to pressure sources. It will also be appreciated by those of ordinary skill in the art that unless otherwise indicated herein, the particular sequence of steps described is illustrative only and can be varied without departing from the spirit of the invention. The systems 10 and 10' of FIGS. 1A and 1B, respectively, are used in the description of the exemplary methods.

The process commences in step 300, following which a predetermined volume of sample is supplied into the feed reservoir 114 at step 302. In step 304 the feed and retentate reservoirs 114 and 116 (or alternatively the feed and permeate reservoirs 114 and 118) are connected to two of the pressure sources 132, 134 and 138. It is understood that either positive pressure sources, for example, pumps or pressurized gas can be used or alternatively vacuum sources can be used as described in Table I.

In step 306, the first pressure differential is applied, and in step 308, the second pressure differential is applied. In one embodiment, both pressure differentials are applied substantially simultaneously. The pressure differentials induce a positive and controllable TMP and TCP. If feed displacement is used as a means of recovering the residual liquid within the flow channel, processing continues at step 330 otherwise, processing of the sample continues in step 310 until the sample is substantially consumed and the desired conversion is achieved. In one embodiment, substantial consumption is about 95% consumed. The processing time is proportional to $\sigma_M$ and, in one embodiment, $\sigma_M$ is greater than about 2 cm$^{-1}$. Although in one embodiment the pressure differentials are adjustable, it is not required that the pressure differentials be changed during the process. In some embodiments the ratio of $\sigma_M$ to $\sigma_1$ is greater than about 1, greater than about 3, and often greater than about 10.

In step 312, the pressure differentials are dissipated by substantially reducing to zero the applied pressures, disconnecting, or shutting off the first and second pressure sources. One of several possible methods are then used to recover the permeate fraction or retentate fraction. The method is selected, for example, based on simplicity and degree of recovery desired. In step 314, the permeate fraction is directly withdrawn from the permeate reservoir 118 and the process is finished in step 340. In step 316, the retentate fraction is directly withdrawn from the retentate reservoir 116 and the process is finished in step 340. Withdrawal of the samples can be accomplished by means of a manual or automatic syringe or pipette, or alternatively by pouring the contents of the reservoir into another container.

In step 320, the retentate is utilized as the displacement medium by inducing a reverse flow by applying a small negative TCP after the feed sample is substantially consumed. The negative TCP causes the retentate to flow toward the feed reservoir 114 thereby displacing the residual fluid within the flow channel 106 towards the feed reservoir 114. The residual liquid, together with the retentate (the displacement medium) is collected in the feed reservoir 114 (where further optional processing steps can occur) and withdrawn in step 322 and the process is finished in step 340. The optional processing steps include subjecting the recovered permeate and retentate fractions to chemical or physical processing steps and in-situ analysis before withdrawal.

In step 324, a small volume of a buffer solution is utilized (e.g., a buffer chase) as the displacement medium. A buffer solution is introduced into the feed reservoir 114 after the feed sample is substantially consumed, followed by the application of a small positive TCP to displace the residual fluid within the flow channel 106. The residual liquid, together with the buffer displacement medium is collected in the retentate reservoir 116, in step 336. In step 328, the retentate is withdrawn from the retentate reservoir 116. In an alternative embodiment, the buffer chase is introduced into the retentate reservoir, followed by the application of a small negative TCP to collect the residual liquid and buffer chase in the feed reservoir 114.

In step 326, the permeate is utilized as the displacement medium by inducing reverse permeation by applying a third pressure differential between the permeate and retentate reservoirs to induce a small negative TMP after the feed sample is substantially consumed. The negative TMP causes a small amount of permeate to flow into the interior of the flow channel thereby displacing the residual fluid within the flow channel 106 by reverse permeation. The residual liquid, together with the small amount of permeate displacement medium is collected in the retentate reservoir 116 and withdrawn in step 328 and the process is finished in step 340. In an alternative embodiment, an osmotic pressure differential existing between the permeate and the residual liquid can be used to induce reverse permeation without the application of a negative TMP. In another alternative embodiment, the residual liquid, together with the small amount of permeate displacement medium is collected in the feed reservoir by applying a third pressure differential between the permeate and feed reservoirs.

The feed displacement method proceeds in step 330, where a small amount of the remaining feed sample is utilized as the displacement medium. The permeation process is stopped before the feed sample is fully consumed by reducing the pressure differentials while there is still some feed sample left in the feed reservoir. In step 332, the pressure differentials are dissipated by disconnecting or shutting off the first and second pressure sources. In step 334, a small flow displaces the residual liquid within the channel towards the retentate reservoir 116. The flow is induced by applying a small positive TCP. The residual liquid, together with the residual feed sample displacement medium is collected in the retentate reservoir 116 in step 336 and withdrawn from the retentate reservoir 116 in step 328. The process finishes in step 340.

From the foregoing, it can be appreciated that the modules and methods of the invention facilitate sample processing using SPF operation. The invention will be further described in the following examples, which are not exhaustive and do not limit the scope of the invention described in the claims.

Examples 1A and 1B

The following two examples illustrate experiments in which pressure sources were used to drive the filtration using the instrumented sample preparation system similar to system 200 of FIG. 5A.

Test Solutions

A bovine serum albumin (BSA) solution was prepared at a concentration of 10 mg/ml in 0.025 M Tris-HCl Buffer adjusted to pH 7.6. All experiments were conducted at room temperature. The BSA was obtained from Sigma-Aldrich, catalog number A-3294.

SPF Modules

SPF modules 190 were made with separation elements 194 comprising hollow fiber membranes. Hollow fiber membranes were polysulfone with a 10,000 MWCO. The separation elements 194 were constructed by potting the hollow fiber membranes into a ⅛" ID clear Tygon™ tubing with a 5-minute epoxy. Modules were made with varying lengths and varying number of polysulfone hollow fiber membranes. Separation elements had two permeate ports (the second port not shown) to allow effective flushing of the permeate compartment. Permeate ports were located within 1 cm of the potted regions to minimize dead volume. Prior to SPF testing, all separation elements were pre-treated and integrity tested as follows:

1. flushed with 1 ml of a 60/40 ethanol/DI-water solution to assure complete wetting;
2. thoroughly flushed with DI-water;
3. integrity tested at 25 psi with compressed $N_2$ using the test set-up described below; and
4. flushed with 0.025 M Tris-HCl buffer.

Test Set-Up

The test system 230 was configured as illustrated in FIG. 5A. Compressed $N_2$ was used as the pressure source 202, the main system pressure regulated with a conventional 0-50 psi pressure regulator 204. Feed and retentate pressures were precisely controlled by means of precision pressure regulators 206 and 210 (0-30 psi, 20-turn pressure regulators), and monitored by precision digital pressure gauges 208 and 212 (0-30 psi, 0.01 psi resolution). The permeate compartment was maintained at atmospheric pressure, while the retentate valve 214 is closed, therefore the test TMP was equal to the feed pressure 208.

Feed and retentate reservoirs comprised ⅛" and 1/16" ID clear Tygon tubing, respectively. The progress of the ultrafiltration experiment was monitored by measuring the length of the liquid column in the reservoirs, the feed reservoir 114 containing approximately 80 microliters per centimeter of length and the retentate reservoir 116 containing approximately 20 microliters per centimeter of length. The retentate was collected at the end of the run in 5 milliliter, pre-tared sample vials, followed by UV assay to determine protein concentration.

Protein Determination

A tabletop UV spectrophotometer, Bausch & Lomb Model Spectronic 21 at 280 nm was used to measure the protein concentration in the feed sample, and in the retentate and permeate fractions. This data was used to determine the concentration factor (ratio of retentate to feed concentration) and the BSA recovery in the retentate (ratio of retentate to feed BSA mass). Multiple dilutions (10:1, 20:1 and 50:1) were conducted on feed and retentate samples, as necessary, to obtain UV spec readings between 0.500 and 1.500 Absorbance Units (AU), and preferably between 0.500 and 1.000 AU. Depending on the sample volume available, 1 cc or 3 cc cuvettes were used.

Test Procedure

The following steps were used in conjunction with examples 1-4 described below:

1. Shut feed port 126 and retentate port 128 using pinch valves 216 and 214, respectively;
2. Set feed and retentate pressures using regulators 206 and 210;
3. Disconnect graduated feed reservoir 114 and introduce BSA sample using 5 ml BD syringe directly into the disconnected feed reservoir 114;
4. Reconnect feed reservoir 114;
5. Unclamp retentate pinch valve 214 and feed pinch valve 216 substantially simultaneously to start ultrafiltration;
6. Measure feed and retentate liquid columns in respective reservoirs 114 and 118 as a function of time using a stop watch; continue until feed reservoir 114 is emptied;
7. Clamp retentate pinch valve 214 when retentate liquid column starts to accelerate (this happens when the feed liquid column becomes depleted at end of the run);
8. Clamp feed pinch valve 216 soon thereafter;
9. Disconnect feed reservoir 114 (to dissipate pressures); then reconnect;
10. Disconnect retentate reservoir 116;
11. Collect retentate by displacing it with $N_2$ into a pre-tared sample vial;
12. Flush module with 2 ml buffer between runs; and
13. Measure BSA concentration of retentate.

Figure 9A:
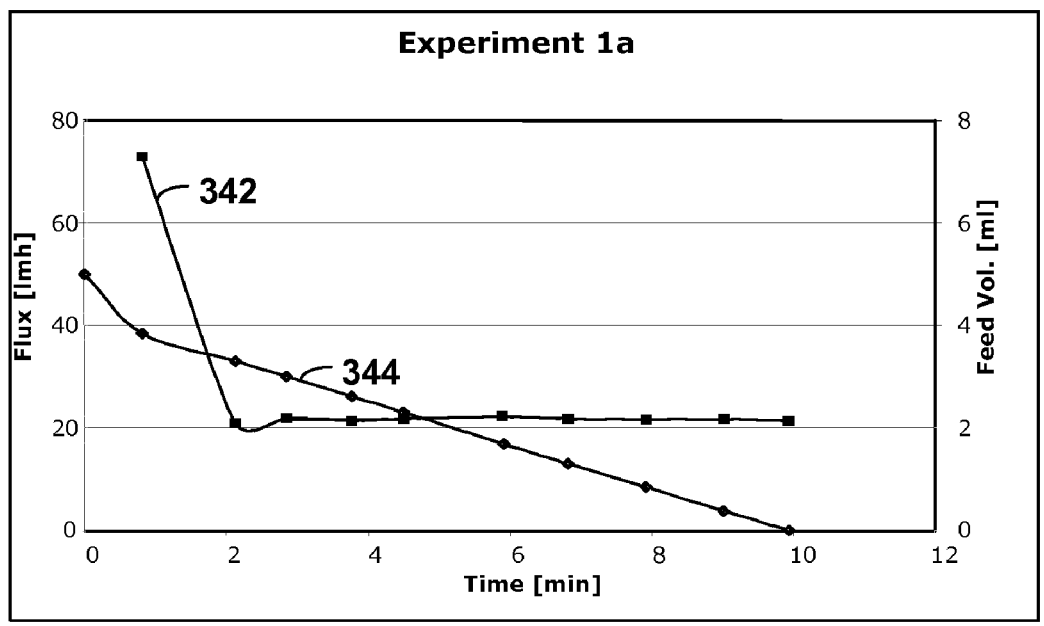
FIGS. 9A and 9B are graphs of flux and conversion vs. time for Example 1A.
Figure 9B:
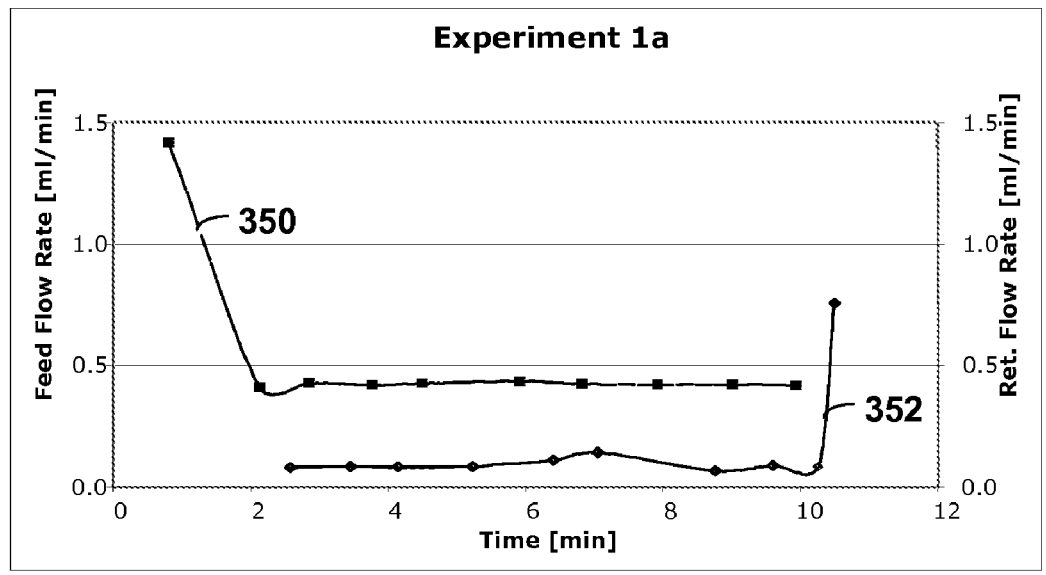

In some experiments the retentate was collected in the retentate reservoir, in others in the feed reservoir. In some cases, a buffer chase was used to displace the residual liquid within the flow channel. In examples 1A and 1B an SPF module with 135 μm hollow fiber membranes in a 3-volume device similar to the sample preparation module 190 of FIG. 5A was used with positive pressure sources to drive a single-pass ultrafiltration. These examples illustrate the concentration of 10 mg/ml BSA using 10,000 MWCO hollow fibers with lumen diameter of about 135 μm and 27.5 cm long. The hollow fibers were obtained from Spectrum Laboratories, Rancho Domingo, Calif. The separation element 194 used in the SPF module 192 comprised a bundle of 10 hollow fiber membranes, having a total membrane area of about 11.7 cm². The feed stream comprised 5 ml of BSA solution. The feed pressure was about 14.60 psi, and the retentate pressure was about 13.05, resulting in a TCP of about 1.55 psi. The retentate was recovered in the feed reservoir; no buffer chase was used. The total retentate mass was about 0.9166 g, corresponding to a conversion of 82%. FIGS. 9A and 9B summarize the data. The flux 342 and the volume of the feed sample 344 are shown as a function of time in FIG. 9A, and the feed flow rate 350 and retentate flow rate 352 as a function of time in FIG. 9B.

Figure 10A:
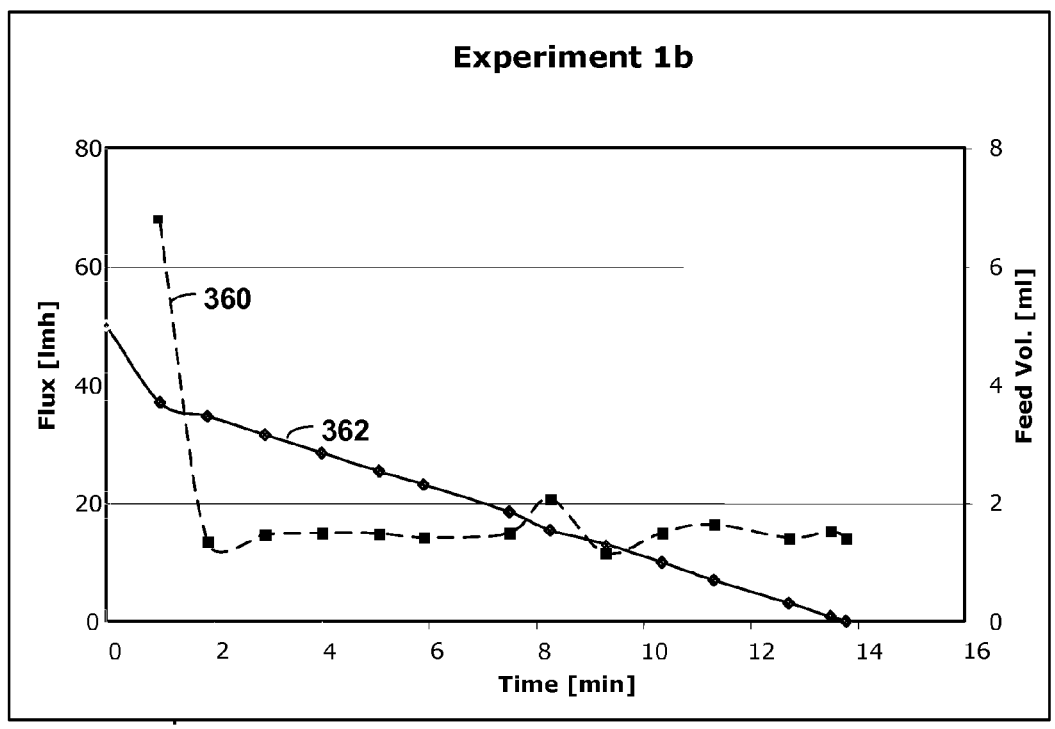
FIGS. 10A and 10B are graphs of flux and conversion vs. time for Example 1B.
Figure 10B:
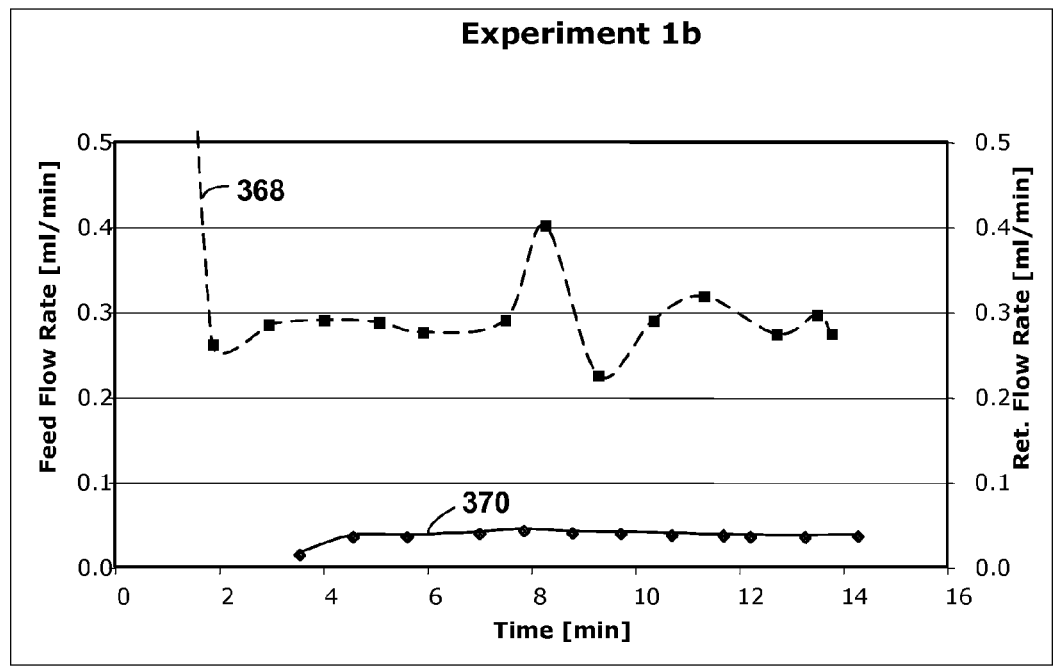

A second run identical to the first was conducted, except that the TCP was lowered to 1.13 psi, and the retentate was collected in the retentate reservoir. The total retentate mass was about 0.4879 g, corresponding to a conversion of 90%. FIGS. 10A and 10B summarize the data. The flux 360 and the volume of the feed sample 362 are shown as a function of time in FIG. 10A, and the feed flow rate 368 and retentate flow rate 370 as a function of time in FIG. 10B.

High steady-state fluxes of 21.7 and 14.9 lmh, respectively, were obtained. Also, as shown in FIGS. 9A, 9B, 10A and 10B, steady state was reached within about 2 minutes, which compares favorably with a calculated transient time of about 1.3 minutes. It was observed that the system pressure was controllable to ±0.02 psi, and, as expected, the conversion can be readily controlled with TCP, the higher the TCP the lower the conversion. A comparative summary of the two runs is shown in table 2 below.

TABLE 2

| Example # | TCP [psi] | $V_0$ [cm/s] | Steady State Flux [lmh] | Retentate Mass [g] | Conversion [%] |
|---|---|---|---|---|---|
| 1A | 1.55 | 5.54 | 21.7 | 0.9166 | 82% |
| 1B | 1.13 | 4.23 | 14.9 | 0.4879 | 90% |

Table 3 below summarizes the parameters for these two runs. The hollow fiber module had a specific membrane area of the channel, $\sigma_C$, of 148 cm$^{-1}$ and a dimensionless length of 4,070. The process was operated at a specific membrane area of the sample, $\sigma_M$, of 2.33 cm$^{-1}$ for both runs 1A and 1B. Here $\sigma_1$ was approximately equal to $\sigma_M$, because the feed reservoir was full.

TABLE 3

| Example # | Time [min] | $\sigma_C$ [cm$^{-1}$] | $\sigma_M$ [cm$^{-1}$] | $\lambda$ [ ] |
|---|---|---|---|---|
| 1A | 10.5 | 148 | 2.33 | 4.070 |
| 1B | 14.3 | 148 | 2.33 | 4.070 |

Examples 2A, 2B and 2C

The following examples compare SPF UF processing with 600 μm HF Membrane to prior art centrifugal devices to demonstrate the slower performance of prior art centrifuge techniques for processing of laboratory scale samples. Examples 2A and 2B provide data on a method of processing of a 3-volume embodiment of the present invention utilizing pressure sources to drive the single-pass ultrafiltration. These examples illustrate the concentration of 10 mg/ml BSA using 10,000 MWCO hollow fibers with lumen diameter of about 600 μm and 155 cm long. In contrast, Example 2C provides data on a method of the prior art utilizing a centrifugal device, Microcon 30, manufactured by Millipore Corp., Billerica Mass., USA.

In examples 2A and 2B, the separation element used in the SPF module comprised a single hollow fiber membrane, having a membrane area of about 29 cm². The feed stream comprised of about 5 ml of BSA solution (exact weight shown in Table 4 below); the feed pressure was about 13.6 psi; the retentate was recovered in the retentate reservoir; and a buffer chase of about 0.5 ml, introduced as described in step 324 of FIG. 8, was used to displace the residual liquid.

In example 2C, the Microcon 30 centrifugal UF device has a circular flat-sheet membrane, with a MWCO of 30,000 Daltons and area of about 0.34 cm². The feed stream comprised about 0.5 ml of BSA solution (exact weight shown in table below); the centrifuge (VWR Scientific Model V) was spun at a velocity of 9,500 RPM, generating an acceleration of about 5,000 g; the retentate was recovered following the recommended procedure, namely, by inverting the feed reservoir (containing the UF membrane) and collecting it in an eppendorf tube; and a buffer chase of about 0.064 ml, added to the feed reservoir and recovered in the same manner as the retentate, was used to displace any residual liquid remaining on the surface of the membrane.

The data from all 3 experiments is summarized in Table 4 below.

TABLE 4

|  | Example 2A | Example 2B | Example 2C |
|---|---|---|---|
| Membrane Area [cm²] | 29 | 29 | 0.34 |
| Mass of Feed Solution [g] | 4.98 | 5.18 | 0.485 |
| Feed Pressure [psig]/[g's] | 13.6 | 13.6 | 5,000 g |
| TCP [psi] | 0.40 | 1.00 | — |
| Permeation Time [min] | 7.5 | 5.5 | 22.0 |
| Conversion [%] (Including Buffer Chase) | 94.1 | 93.3 | 94.1 |
| Recovery [%] (Retentate Only) | 85.1 | 83.7 | 92.6 |
| Recovery [%] (Retentate + Buffer Chase) | 95.8 | 94.7 | 93.4 |
| Permeate Loss [%] | — | 0.8 | 2.4 |
| Average Flux [lmh] | 13.3 | 18.7 | 12.4 |

The SPF module 190 processed the sample in less than 10 minutes compared to more than 20 minutes for the prior art centrifugal device; this difference is believed to be due to the high $\sigma_M$ of about 6 cm$^{-1}$ for the SPF embodiment as compared to a $\sigma_M$ of less than 1 cm$^{-1}$ for the prior art centrifugal device. All devices yielded very high BSA recovery, exceeding 90%. Table 5 below summarizes other method and device parameters for these three runs. Note that for the prior art device $\sigma_C$ and $\lambda$ are undefined since these devices do not have flow channels.

TABLE 5

| Example # | Time [min] | $\sigma_C$ [cm$^{-1}$] | $\sigma_M$ [cm$^{-1}$] | $\lambda$ [ ] |
|---|---|---|---|---|
| 2A | 7.5 | 67 | 5.8 | 10,300 |
| 2B | 5.5 | 67 | 5.6 | 10,300 |
| 2C | 22.0 | — | 0.7 | — |

Examples 3 and 4

The descriptions of the methods and modules used in examples 1 and 2 apply to examples 3 and 4, except that vacuum sources were used to drive the permeation instead of positive pressure sources. The test set up was accordingly modified as described below. The procedure outlined in examples 1 and 2 was followed with minor adjustments to account for the use of vacuum sources instead of pressure sources.

Test Set-Up

A system similar to system 230 was used for examples 3 and 4 as shown in FIG. 5B. A vacuum pump 232 was used as the vacuum source coupled to the permeate port. The vacuum pump 232 was capable of generating vacuums exceeding 29 in-Hg. The feed port 126 was vented to atmospheric pressure, and therefore the TMP was about 14.7 psi. The retentate pressure, or more precisely, the TCP, was finely regulated by means of the gravity siphon 240, whereby the height of the column of water 242 essentially determines the TCP, the TCP being directly proportional to the height of the column of water 242 (i.e., 26" of water≈1 psi). By adjusting the location of the reservoirs forming the gravity siphon 240 the TCP is controlled within ±0.02 psi.

Example 3

In example 3 an SPF module with 600 µm hollow fiber membranes in a 3-volume device similar to the sample preparation module 192 of FIG. 5B was used with vacuum sources to drive the single-pass ultrafiltration. This example illustrates the concentration of 10 mg/ml BSA using 10,000 MWCO hollow fibers with lumen diameter of about 600 µm and 155 cm long. The module 192 comprised a separation element 194 having a single hollow fiber membrane with an area of about 29 cm². The feed stream comprised of about 5.2 ml of BSA solution; the TCP was about 33 in-H$_2$O, or 1.3 psi; a buffer chase of about 0.1 ml, introduced as described in step 324 of FIG. 8, was used to displace the residual liquid; and the retentate was recovered in the retentate reservoir.

It took about 5.9 minutes to complete the ultrafiltration, producing about 0.427 g of retentate (including the buffer chase), resulting in a conversion of about 92% and an average flux of about 17 lmh. The BSA recovery in the retentate was 98%. The hollow fiber module had a specific membrane area of the channel, $\sigma_C$, of about 67 cm$^{-1}$ and a dimensionless length, $\lambda$, of about 10,300. The process was operated at a specific membrane area of the sample, $\sigma_M$, of 5.9 cm$^{-1}$. The SPF process utilizing vacuum sources performed similarly to the SPF process utilizing pressure sources. No complications were observed, for example out-gassing, resulting from the use of a deep vacuum in the permeate volume.

The following description illustrates results from simulations that use various principles of the present teachings and invention. These simulations are not exhaustive and are not intended to limit the scope of the present invention. Simulations 1 through 4 were calculated predictions based on a one-dimensional, steady-state mathematical model for the ultrafiltration of protein solutions utilizing hollow fiber membranes. The model takes into account the following factors:

1. the osmotic pressure of the protein solution as a function of concentration;
2. the hydraulic permeability of the membrane;
3. the dimensions of the hollow fiber;
4. concentration polarization resulting from the interplay of permeation and radial diffusion of solute transport in circular tubes under laminar flow;
5. the pressure drop along the flow channel; and
6. the increase in solute concentration along the flow channel as a result of permeation.

Numerical integration of the differential equations was performed using MathCAD version 12. Physical properties of BSA found in the technical literature (osmotic pressure, viscosity and diffusion coefficient) were used to perform each simulation. Multiple simulations were done using various conditions of pressures, feed concentration, membrane permeability, hollow fiber dimensions and conversions to illustrate the various aspects of the invention.

Simulation 1

Simulation 1 was performed for a 3-volume device with a HF separation element consisting of 10 flow channels with a lumen diameter of 0.02 cm and a length of 100 cm. The device has a feed reservoir with a 4 cc feed volume and is loaded with a feed sample of about 3 cc. The membrane area of the separation element is about 63 square centimeters, resulting in a value of $\sigma_M$ for the method of about 21 cm$^{-1}$, a value of $\sigma_1$ and $\sigma_C$ for the device of about 16 and 200 cm$^{-1}$, respectively, and a $\sigma_C$-to-$\sigma_1$ ratio for the device of about 13. The simulation results in the following prediction: a single-pass conversion of about 90% can be achieved in a period of about 2 minutes.

Simulation 2

Simulation 2 was performed, similar to simulation 1 except that the device had only one flow channel, a feed reservoir with a 1 cc feed volume, and is loaded with a feed sample of about 0.3 cc. The membrane area of the separation element is about 6.3 square centimeters, resulting in a value of $\sigma_M$ for the method of about 21 cm$^{-1}$, a value of $\sigma_1$ and $\sigma_C$ for the device of about 6 and 200 cm$^{-1}$, respectively, and a $\sigma_C$-to-$\sigma_1$ ratio for the device of about 33. The simulation results in the following prediction: a single-pass conversion of about 90% can be achieved in a period of about 2 minutes. Additional simulations 2A and 2B illustrating the use of the quantitative parameter α in equation 7 were performed for a 3-volume device with a HF separation element consisting of 10 flow channels with a lumen diameter of 0.04 cm and a length, L, of 100 cm. The device has a feed reservoir with a 4 cc feed volume and is loaded with a feed sample of about 3 cc. The membrane area of the separation element is about 126 square centimeters, resulting in a value of $\sigma_M$ for the method of about 42 cm$^{-1}$, and a value of $\sigma_1$ and $\sigma_C$ for the device of about 32 and 100 cm$^{-1}$, respectively. The value of α is about 15,400. The simulation results in the following prediction: with a TCP of about 0.03 Bar a single-pass conversion of about 90% can be achieved in a period of about 2 minutes. A second simulation was performed on a 3-volume device with a HF separation element consisting of one flow channel with a lumen diameter of 0.02 cm and a length, L, of 100 cm. The device has a feed reservoir with a 1 cc feed volume and is loaded with a feed sample of about 0.3 cc. The membrane area of the separation element is about 6.3 square centimeters, resulting in a value of $\sigma_M$ for the method of about 21 cm$^{-1}$, and a value of $\sigma_1$ and $\sigma_C$ for the device of about 6.3 and 200 cm$^{-1}$, respectively. The value of α is about 30,900. The simulation results in the following prediction: with a TCP of about 0.2 Bar a single-pass conversion of about 90% can be achieved in a period of about 2 minutes.

Simulation 3

A simulation was performed for a 3-volume device in a centrifugal field with an acceleration of about 2,000 g using a HF separation element consisting of 2 flow channels with a lumen diameter of 0.02 cm and a length of 100 cm. The device has a feed reservoir with a 4 cc feed volume and is loaded with a feed sample of about 3 cc. The separation element is located about 1.02 cm below the feed sample reservoir and the retentate reservoir is located about 0.73 cm below the feed sample reservoir. The membrane area of the separation element is about 6.3 square centimeters, resulting in a value of $\sigma_M$ for the method of about 2 cm$^{-1}$, and a value of $\sigma_1$ and $\sigma_C$ for the device of about 1.6 and 200 cm$^{-1}$, respectively. The simulation results in the following prediction: the TCP is about 0.03 bar, and a single-pass conversion of about 95% can be achieved in a period of about 13 minutes.

Simulation 4

A simulation was performed for a 3-volume device comprising a feed reservoir with a feed volume of about 4 cc and a HF separation element consisting of 10 flow channels with a lumen diameter of 0.03 cm and a length of 150 cm. The feed reservoir is loaded with about 3 cc of a feed sample and is vented to atmospheric pressure, while the retentate and permeate reservoirs are connected to vacuum sources at about 0.9 and 0.05 bar-absolute, respectively. On application of these pressures the filtration process starts. When about 0.5 cc of sample is left in the feed reservoir, the permeate reservoir is vented to atmospheric pressure and the vacuum source connected to the retentate reservoir is raised to about 0.95 bar-absolute. The permeation process is thereby substantially stopped while the remaining 0.5 cc of feed sample flows along the hollow fiber lumen by virtue of the TCP (at about 0.05 bar), thereby displacing the residual liquid contained within the channel volume. The value of $\sigma_1$ and $\sigma_C$ for this device are about 35 and 133 cm$^{-1}$, respectively, and the value of $\sigma_M$ for the method is about 47 cm$^{-1}$. The simulation results in the following prediction: a single-pass conversion of about 90% is achieved in a period of about 1.5 minutes with over 90% recovery of the retained species.

Figure 11A:
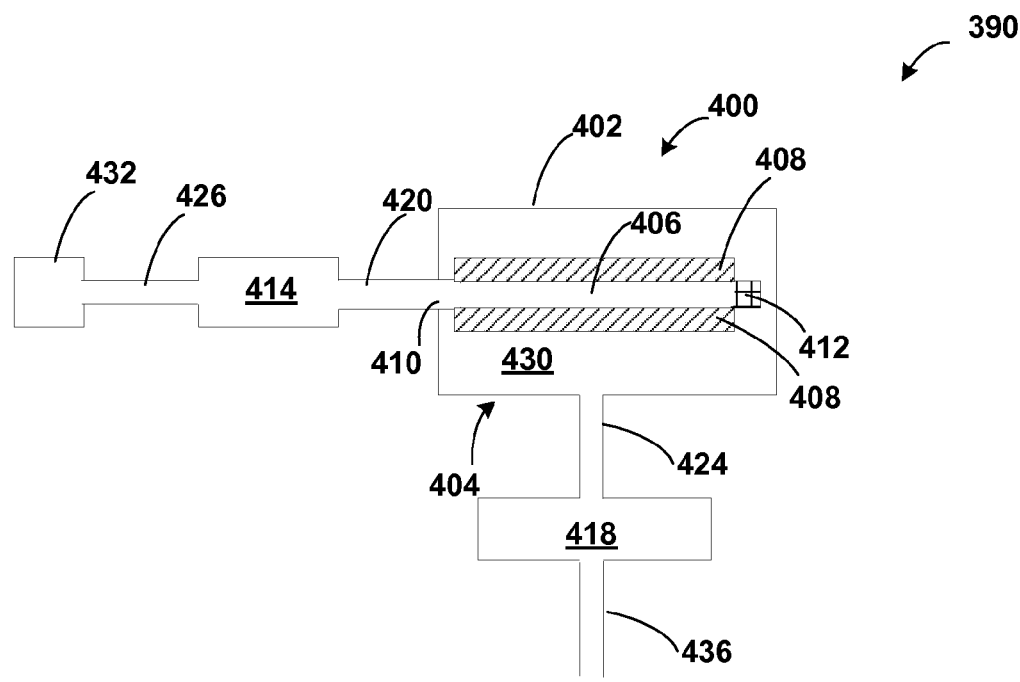
FIGS. 11A and 11B are schematic diagrams of 2-volume devices including hydrophobic vents according to the invention.

Now turning to FIG. 11A, a sample preparation system 390 includes a 2-volume sample preparation module 400 comprising a housing 402, a separation element 404 disposed within the housing 402 comprising a permeate compartment 430 and at least one flow channel 406 having an inlet 410, an outlet 412 and a surface comprising a filtration membrane 408. The 2-volume module 400 is useful when the desired result of processing a sample is the permeate fraction. The module 400 further comprises a feed reservoir 414 fluidly coupled to the channel inlet 410 through a feed flow passage 420, a hydrophobic vent 412 affixed to the channel 406 distally from the inlet 410 and a permeate reservoir 418 fluidly coupled to the separation element 404 through a permeate flow passage 424. In one embodiment the hydrophobic vent 412 is disposed at the end of the channel 406, and in another embodiment the hydrophobic vent 412 forms a portion of the flow channel 406. The system 390 further includes a feed pressure source 432 coupled to the module 400. The module 400 additionally comprises a feed port 426 coupled to the feed reservoir 414 coupled to the feed pressure source 432, and a permeate port 436 coupled to the permeate reservoir 418. It will be appreciated that the position of the hydrophobic vent 412 can vary at the distal end of the channel 406, for example the vent 412 can be located along the walls of the channel 406 instead of the end of the channel 406.

In operation, the feed port 426 is used to introduce the feed sample into the feed reservoir 414 and then to connect the feed pressure source 432 to the feed reservoir 414. The feed pressure is set to a pressure to provide a positive pressure differential between the feed port 426 and the permeate port 436. Here, the permeate reservoir 418 is vented to the atmosphere. The pressure differential provides the necessary driving forces for tangential flow by inducing the TCP and for permeation by inducing the TMP. Timed application of this pressure differential controls the conversion of the liquid sample volume in the feed reservoir 414 into the permeate volume in the permeate reservoir 418. When the sample processing is completed, the permeate can be withdrawn through the permeate port 436. Other methods of recovering the sample fractions are described below in conjunction with FIG. 15. The pressure differential is provided by a pressure source, vacuum source, or by the application of centrifugal acceleration. It is noted that 2-volume modules need only one pressure or one vacuum source, said source being utilized to create the TMP, thereby inducing the permeation through the membrane. The second pressure differential, the TCP, is created by the tangential flow induced in the flow channel by the permeation, and is therefore, not directly controlled.

A practical consideration in the sample-preparation devices of the present invention is that it may be desirable to have the volume of the feed container be greater than the interior volume of the flow channel. This practical consideration implies that the ratio of $\sigma_C$ to $\sigma_1$ should be greater than about 1.0, preferably greater than about 3.0, and more preferably greater than about 10. In various embodiments, it may be convenient for the TCP to be greater than about 0.02 psi, e.g. to facilitate control of the TCP. In various embodiments, it has been discovered that this goal can be realized if the device design and method meets the following relationship: $\alpha > 10,000$.

Figure 11B:
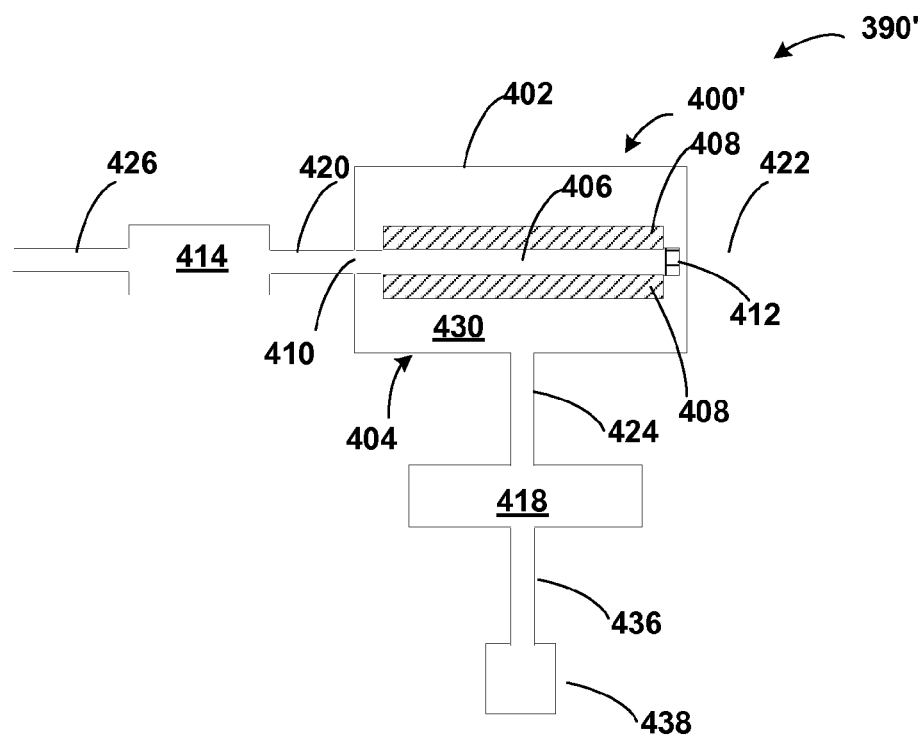

Now referring to FIG. 11B, in which like elements are provided having like reference designations as in FIG. 11A, a sample preparation system 390' includes a 2-volume sample preparation module 400' similar to module 400 of FIG. 11A and a pressure source 438 coupled to the permeate reservoir 418 via the permeate port 436. In addition, the feed reservoir 414 is vented to the atmosphere instead of being coupled to pressure source 432. In one embodiment, pressure source 438 is a vacuum pump which provides a positive pressure differential between the feed port 426 and the permeate port 436. In an alternative embodiment of modules 400 and 400', it is advantageous to utilize both pressure and vacuum sources connected to the feed reservoir 414 and permeate reservoir 418. In one embodiment, sample preparation system 390' can process a sample in less than about 10 minutes and generate conversions exceeding about 90% with retentate pressures between about 0.5 and about 0.98 Bar absolute; permeate pressures typically about 0.1 Bar absolute; resulting in a TMP of about 0.9 Bar and a TCP of about 0.02 to about 0.5 Bar.

While it is possible to operate the 2-volume modules 400 and 400' without a hydrophobic vent 412, the use of the hydrophobic vent 412 facilitates the operation of 2-volume modules by venting of gases present within the flow channel at the start of permeation and facilitating the recovery of residual permeate or retentate at the end of permeation, which can be accomplished, for example, by inducing a (positive) pressure differential between the permeate and the feed reservoirs. In some embodiments, the hydrophobic vent provides these operational benefits by fluidly connecting the interior of the flow channel to the permeate reservoir.

Figure 12:
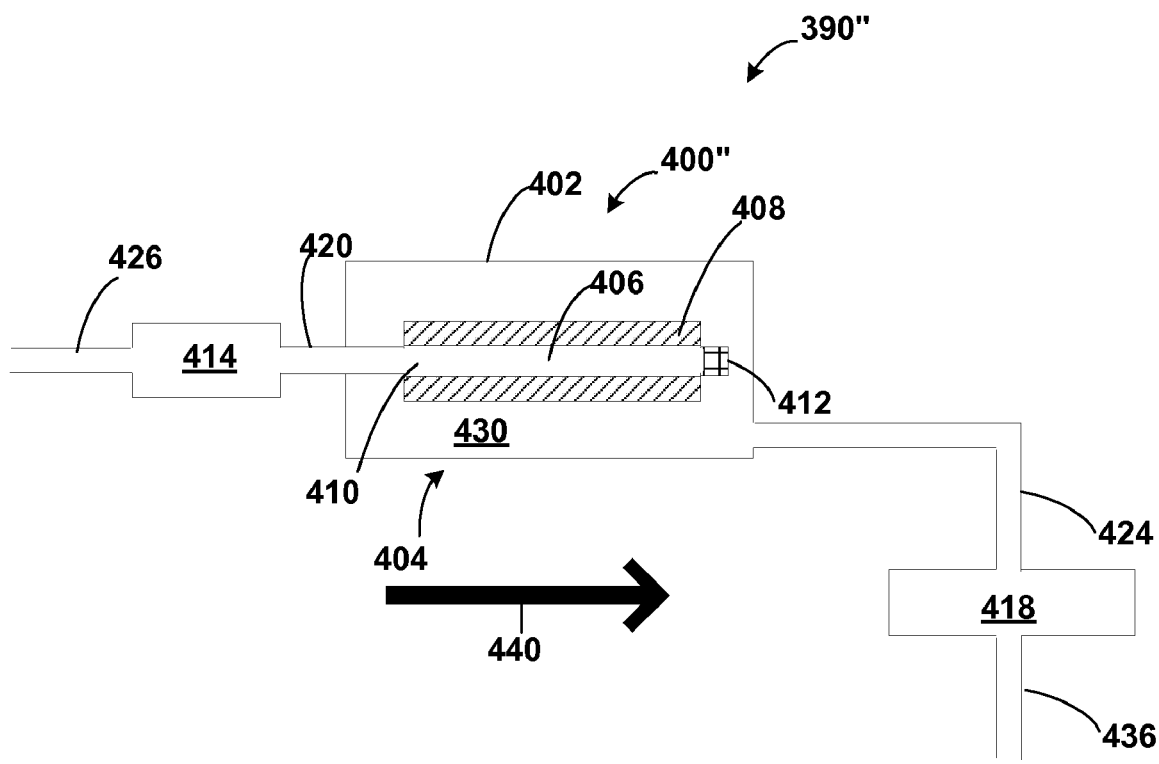
FIG. 12 is a schematic diagram of a 2-volume device similar to the devices of FIG. 11A suitable for operation in a centrifuge.

Now referring to FIG. 12, in which like elements are provided having like reference designations as in FIG. 11A, a sample preparation system 390" includes a 2-volume sample preparation module 400" similar to module 400 of FIG. 11A. Here, system 390" does not include any directly coupled pressure sources. The feed reservoir 414, and permeate reservoir 418 are vented to the atmosphere instead of being coupled to pressure sources. Here, the driving forces are provided by a centrifuge (not shown) with a centrifugal acceleration vector indicated by arrow 440. The feed reservoir 414 and the permeate reservoir 118 are juxtaposed along the centrifugal acceleration vector 440, the feed reservoir 414 and the permeate reservoir 418 at opposite ends of the centrifugal acceleration vector 440. In one embodiment, the specific membrane area of the flow channel 406 is greater than about 80 cm$^{-1}$ and the specific membrane area of the module, $\sigma_1$, is greater than about 2 cm$^{-1}$.

In operation, the centrifuge provides the pressure differential driving forces. The location and orientation of the feed reservoir 414, the permeate reservoir 418 and the separation element 404 with respect to the centrifugal acceleration vector 440 determine the TCP and TMP. In various embodiments, the relative location of the separation element 404 provides the ability to control induced TCP substantially independently of the induced TMP by locating the hydrophobic vent 412 relative to the average location of the membrane in the separation element 404. The ports 426 and 436, and flow passages 420 and 424 provide for adding and removing liquids as well as venting to the atmosphere and the location of these ports and passages as shown in FIG. 12 is not intended to limit the invention in any way. Vacuum and other pressure sources could be optionally used for recovery if desired.

In certain embodiments of the sample-preparation modules utilizing a centrifugal driving force, as exemplified in FIGS. 2 and 12, a difference in the position of the feed and retentate reservoirs, e.g., of about 2 to 4 mm with respect to the direction of the acceleration vector can induce the TCP necessary to create tangential flow. A larger difference in the position between the feed and the permeate volume, e.g., of about 1 centimeter being adequate to induce the TMP necessary to create permeation if the centrifugal acceleration is about 1,000 g.

Figure 13:
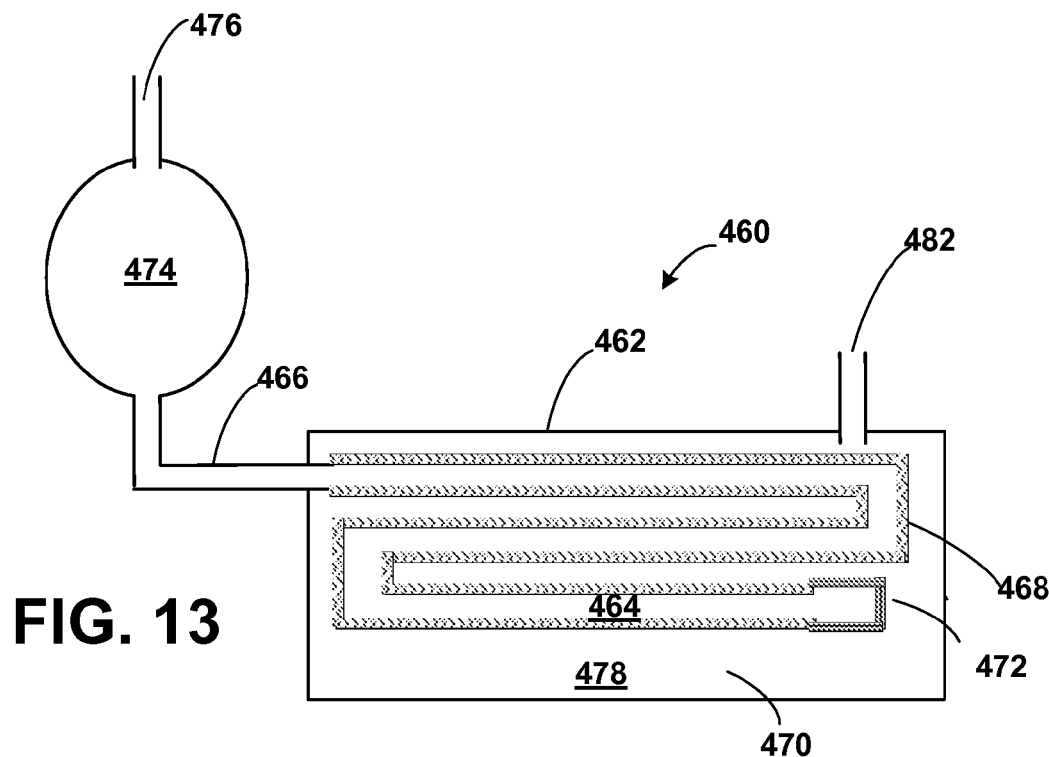
FIG. 13 is a schematic diagram of 2-volume device including a hydrophobic vent in which the separation element is integrated into the permeate reservoir according to the invention.

Referring to FIG. 13 a 2-volume sample preparation module 460 similar to module 400 of FIG. 11A includes a housing 462, a permeate reservoir 470, a permeate port 482 fluidly coupled to the permeate reservoir 470, and a separation element 478 which is integrated within the permeate reservoir 470. The separation element 478 includes flow channel 464 and membrane 468. The module 460 further includes a feed reservoir 474, a feed passage 466 fluidly coupled to the flow channel 464 and the feed reservoir 474, and a feed port 476 fluidly coupled to the feed reservoir 474. In operation, a sample is supplied through feed port 476 and a positive pressure source (not shown) is connected to the feed reservoir 474 through feed port 476 to drive permeation. Alternatively, a vacuum source is connected to the permeate reservoir 470 through port 482 to drive permeation. The permeate port 482 is used recover the permeate.

Figure 14:
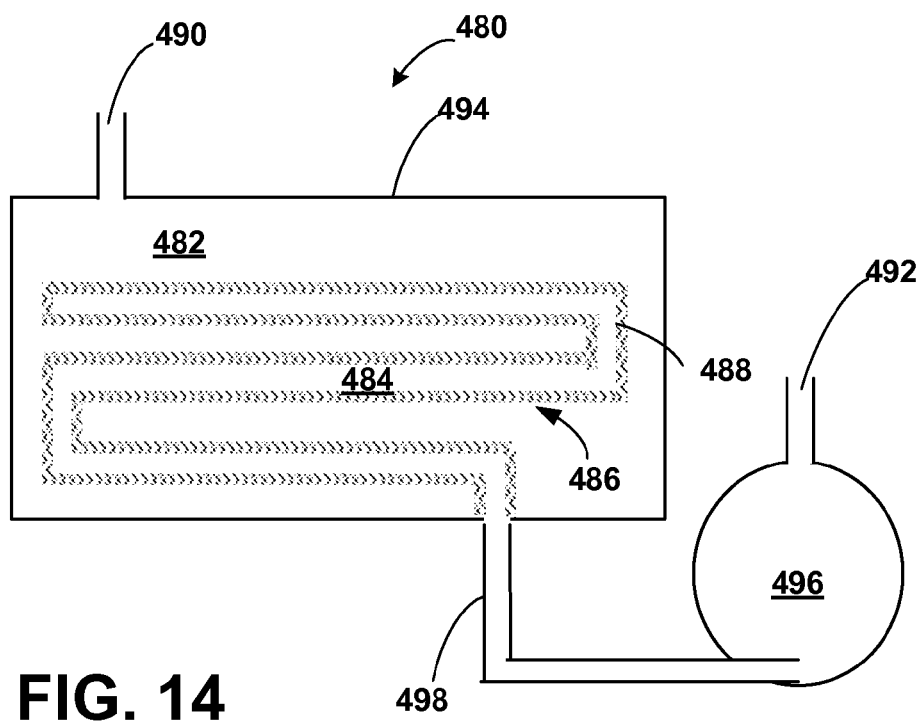
FIG. 14 is a schematic diagram of a 2-volume device in which the flow channel carries the permeate to the permeate reservoir and the separation element is integrated into the feed reservoir according to the invention.

In alternative 2-volume embodiments, it is possible for the feed stream to flow on the outside of hollow fiber membranes with the permeate entering the lumen of the hollow fiber membranes and flowing on the inside of the membrane. Referring to FIG. 14, a 2-volume module 480 includes a feed reservoir 482, a permeate reservoir 496, a feed port 490 fluidly coupled to the feed reservoir 482, a permeate port 492 fluidly coupled to the permeate reservoir 496, a permeate passage 498 fluidly coupled to the permeate reservoir 496 and a separation element 486 disposed within the feed reservoir 482. The separation element 486 includes a flow channel 484 having a membrane surface 488 and coupled to the permeate passage 498.

In operation, a sample is supplied through feed port 490 and a positive pressure source (not shown) is connected to the feed reservoir 482 through feed port 490 to drive permeation. Alternatively, a vacuum source is connected to the permeate reservoir 496 through port 492 to drive permeation. Here, the flow channel 484 carries permeate rather than retentate and the interior of the flow channel 484 is in fluid communication with the permeate reservoir. In alternative embodiments, the feed port 490 and the permeate port 492 are used to apply the pressure differential, and the permeate port 492 is used remove the permeate.

Figure 15:
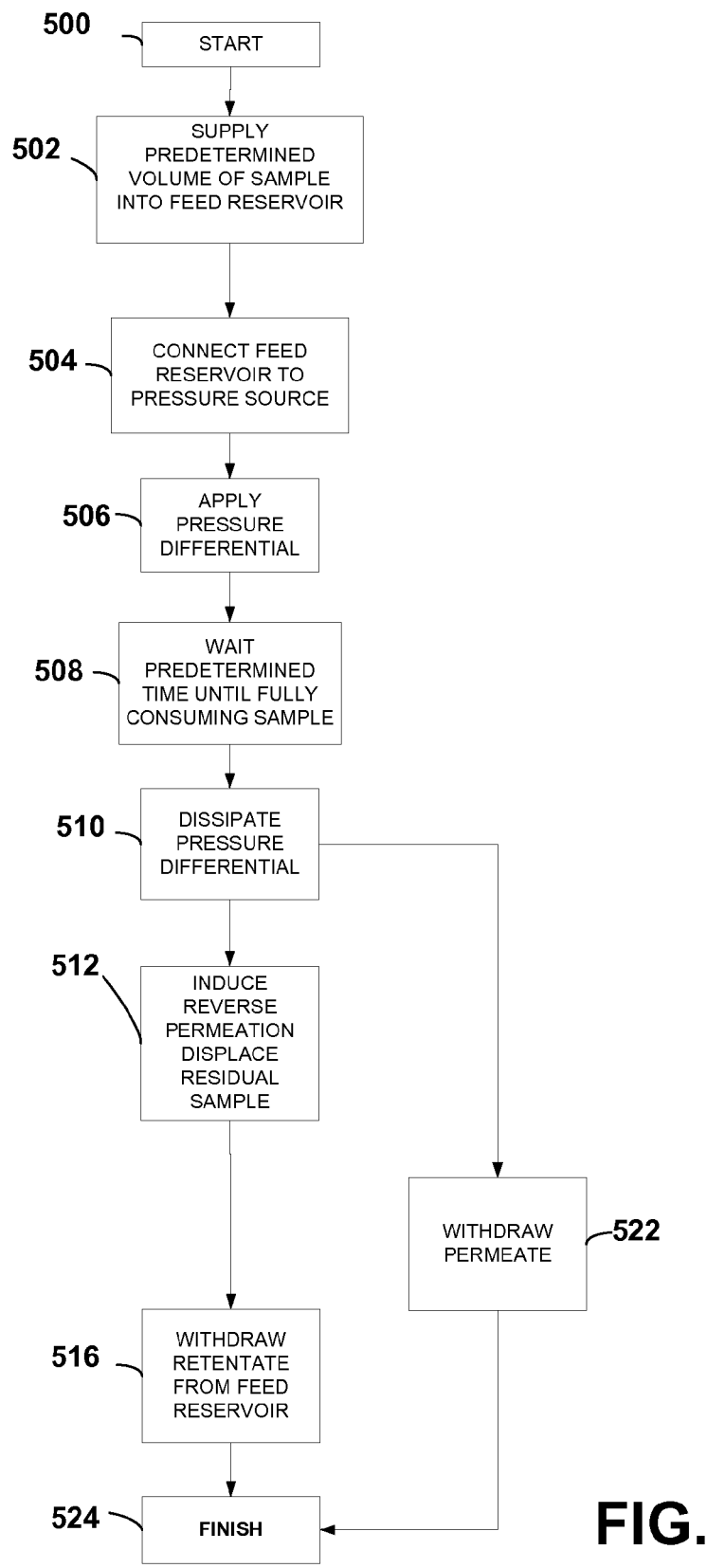
FIG. 15 is a flow diagram illustrating the steps used to process a sample and recover the retentate or permeate fractions using the devices of FIGS. 11A, 11B, and 12.

Turning now to FIG. 15, a flow diagram illustrates a process for processing a sample and recovering the permeate fraction using 2-Volume devices. The systems 400 and 400' of FIGS. 11A and 11B, respectively, are used in explaining the exemplary methods. The process commences in step 500, following which a predetermined volume of sample is supplied into the feed reservoir 414 at step 502. In step 504 the feed reservoir 414 is connected a pressure source 432 (or alternatively permeate reservoir 418 is connected to pressure source 438). It is understood that either positive pressure sources, for example, pumps or pressurized gas can be used or alternatively negative pressure vacuum sources can be used as well as centrifugal forces. Venting through hydrophobic vent 412 occurs at the start of the SPF process to allow displacement of the air present within the flow channel. In step 506, the pressure differential is applied inducing a positive and controllable TMP. Processing of the sample continues in step 508 until the sample is substantially consumed. In step 510, the pressure differential is dissipated by disconnecting or shutting off the pressure source. If a displacement method is being used to recover the retentate, processing continues in step 512 otherwise the permeate fraction is directly withdrawn from the permeate reservoir 418 in step 522 by means of a manual or automatic syringe or pipette, or alternatively by pouring the contents of the reservoir into another container, and the process is finished in step 524.

In another method suitable for 2-volume devices, the residual liquid and small amount of permeate are displaced towards the feed reservoir and then collected from the feed reservoir starting at step 512. In step 512, a portion of the permeate is utilized as the displacement medium by inducing reverse permeation by applying a small negative TMP after the feed sample is substantially consumed. The negative TMP causes a small amount of permeate to flow into the interior of the flow channel thereby displacing the residual fluid within the flow channel 106 by reverse permeation. The residual liquid, together with the small amount of permeate used as the displacement medium) is collected in the feed reservoir 414 and withdrawn in step 516 and the process is finished in step 524. In still another variant to this latter displacement method, suitable for 2-volume devices equipped with a hydrophobic vent 412, pressurized gas in the permeate compartment is utilized to displace the residual liquid back to the feed reservoir 414; the gas displacement medium originating from the permeate reservoir 418 used instead of a liquid.

The invention will be further described in the following example, which is not exhaustive and does not limit the scope of the invention described in the claims.

Example 4

In example 4 an SPF module with a 600 μm hollow fiber membranes in a 2-volume device similar to the sample preparation module 400' of FIG. 11B was used with vacuum sources to drive the SPF ultrafiltration process. This example utilized the same module used in Example 3 with a simulated hydrophobic vent. To simulate the presence of a hydrophobic vent at the distal end of the hollow fiber, an additional "venting" step was added to the test procedure. The venting step comprised filling up of the flow channel with a small amount of the sample prior to the start of permeation (i.e., prior to the application of a full vacuum to the permeate reservoir). This was accomplished by first applying the vacuum from the gravity siphon (about 33 in-H$_2$O, or 1.3 psi) to the retentate reservoir, which aspirated the sample into the flow channel until liquid showed up in the retentate reservoir, at which point the retentate pinch valve 238, located immediately downstream of the module, was shut off. In this manner any gas present within the flow channel is displaced prior to the start of permeation. In the event that the module possessed a hydrophobic vent, the venting would occur automatically without the need for this venting step.

The 2-volume SPF module comprised a separation element made with a single hollow fiber membrane with a lumen diameter of about 600 μm, a length of about 155 cm and an area of about 29 cm². The feed stream comprised of about 5.24 ml of BSA solution, and permeation proceeded until the feed sample was substantially consumed. The retentate was recovered in the feed reservoir by a process similar to step 512 of FIG. 15, as follows: apply a small vacuum of about 1.3 psi (utilizing the gravity siphon as the vacuum source) to the feed reservoir while simultaneously opening the retentate pinch valve to simulate the action of a hydrophobic vent.

The ultrafiltration process took about 7.2 minutes to complete, producing about 0.65 g of retentate, resulting in a conversion of about 88% and an average flux of about 13 lmh. The BSA recovery in the retentate was 86%. Since the volume of the flow channel is about 0.44 ml, it is estimated that about 0.2 ml of liquid permeated back through the membrane (i.e., permeate present in the permeate reservoir) during the dwell time between the end of permeation and the recovery of the permeate. This "reverse permeation" is believed to have been induced by the osmotic pressure of the residual liquid within the flow channel. The hollow fiber module had a specific membrane area of the channel, $\sigma_C$, of about 67 cm$^{-1}$ and a dimensionless length, $\lambda$, of about 10,300. The process was operated at a specific membrane area of the sample, $\sigma_M$, of 5.5 cm$^{-1}$. As expected, the flux of the 2-volume device is about 25% lower than that of a 3-volume device with the same separation element due to the fact that the retentate is accumulated within the flow channel.

Figure 16:
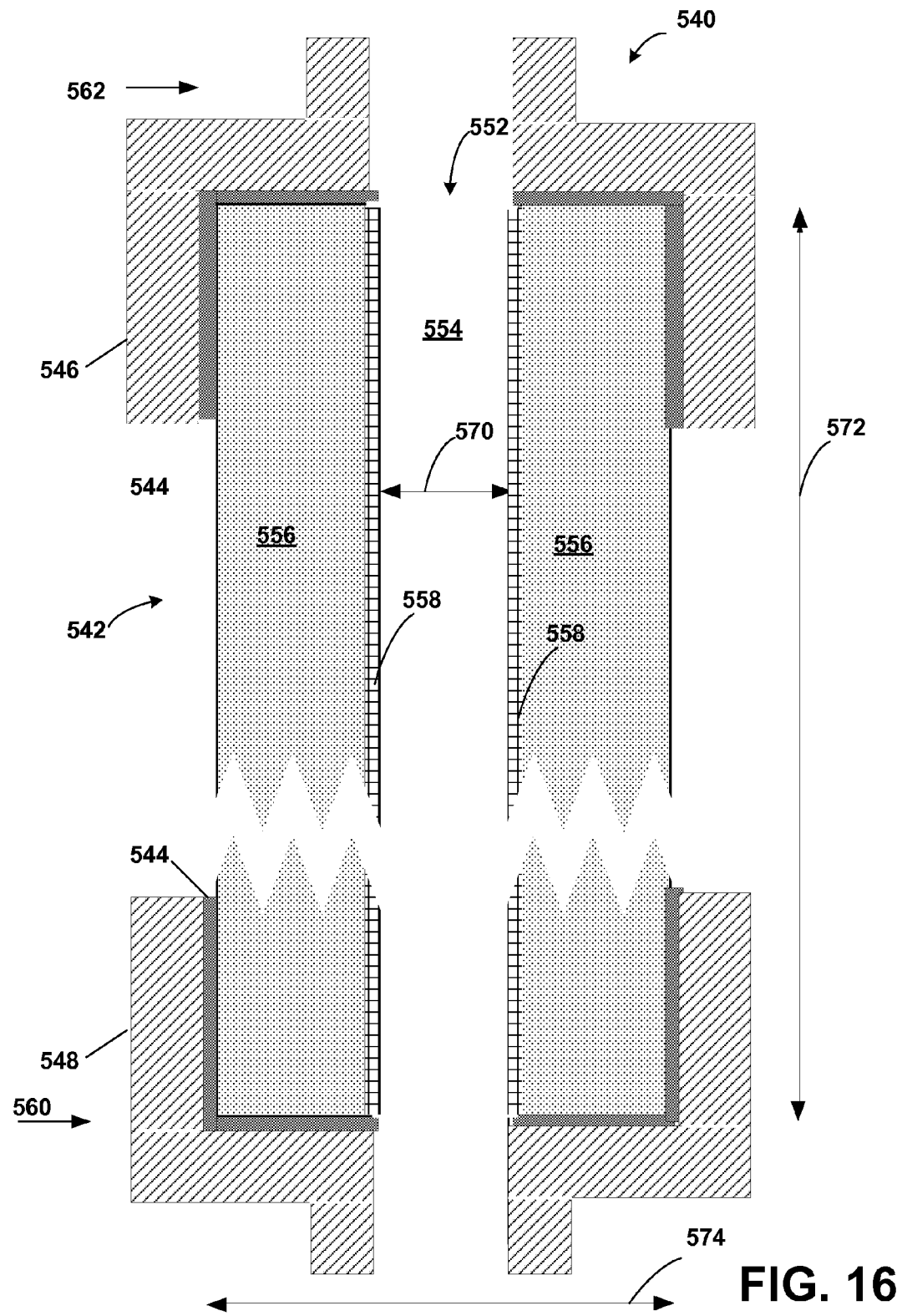
FIG. 16 is a schematic diagram a 2-volume hollow fiber module suited for small volume samples where pressure differentials are induced by capillary forces according to the invention.

Referring to FIG. 16, a 2-volume separation module 540, suitable for very low volume samples (less than 50 μL) where pressure differentials are induced by capillary forces, comprises separation element 542 having a thick-walled hollow fiber membrane 552. The lumen of the hollow fiber membrane 552 forms flow channel 554 and in one embodiment has a diameter 570 of about 100 micrometers and a length 572 of about 6 centimeters. The hollow fiber membrane 552 comprises a hollow fiber wall 556 and an ultrafiltration membrane 558 on the lumen inside diameter supported by the hollow fiber wall 556. The module 540 has a proximal end 560, a distal end 562, and an outside diameter 574, in one embodiment about 350 micrometers. The module 540 further comprises seal 544 and an end cap 546 forming an upper port and end caps 548 forming a lower port. In one embodiment the module 540 has a membrane area of about 0.2 cm² and the hollow fiber wall 556 has a porosity ε between about 0.6 and 0.8.

In operation, the proximal end 560 of module 540 is dipped into sample reservoir (not shown), and the suction created by the capillary action produced by the lumen draws the sample into the flow channel 554 creating a tangential flow. The suction created by the capillarity of the porous structure of the wall 556 causes a portion of the liquid sample to permeate through the ultrafiltration membrane 458. In one embodiment, the void volume of the hollow fiber wall 556 is about 4.5 microliters, and the void volume of the flow channel 554 is about 0.5 microliters, resulting in an about 90% conversion of a 5 microliter feed sample. At the end of the ultrafiltration process the retentate occupies the hollow fiber lumen 552, which can be removed by various methods, for example, by suction with a micro-bore syringe, or by a small centrifugal action. In some applications, a small portion of the retentate is drawn into a subsequent analytical device, for example, a capillary electrophoresis column. In these applications, the tip of the capillary electrophoresis column is inserted into the hollow fiber lumen 552 at the distal end 562, followed by the application of a suitable electromotive force to load the solutes present in the retentate into the capillary electrophoresis column. In these embodiments, $\sigma_M$ is about 40 cm$^{-1}$, $\sigma_c$ is about 200 cm$^{-1}$ and $\lambda$ is about 200. An array of modules 540 can also be used in an automated sample processing systems using sample handling techniques known in the art. In alternative embodiments, the separation element can comprise flat-sheet membranes, microfiltration membranes or membrane monoliths.

In alternative embodiments, the inventive modules can also be used to perform a diafiltration process. In diafiltration, a buffer solution replaces the solution that permeates through the membrane in order to change the composition of the solution in which the retained solutes are dissolved. The addition of the replacement solution can be performed, for example, substantially simultaneously with permeation, sequentially alternating between permeation and diafiltration steps, or in a combination of steps.

It is to be understood that although the preferred embodiments described herein relate specifically to separations of interest in biomolecular applications, the principles, practice and designs described herein are also useful in other applications. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. A module for the filtration of a liquid sample comprising:
   a separation element comprising at least one flow channel having a flow channel inlet disposed at a first end of the flow channel, a flow channel outlet disposed at a second opposite end and a wall having a surface comprising an ultrafiltration membrane;
a feed reservoir fluidly coupled to the flow channel inlet;
a retentate reservoir fluidly coupled to the flow channel outlet;
a permeate reservoir fluidly coupled to the separation element; and
wherein the ratio of the membrane area of the separation element to the volume of the feed reservoir is greater than about 2 cm$^{-1}$.

2. The module of claim 1 wherein the at least one flow channel has a length adapted to provide a relatively large and controllable value of TCP and is characterized by dimensionless parameter, α greater than about 10,000.

3. The module of claim 1 further comprising a first pressure source port coupled to the permeate reservoir and a second pressure source port coupled to the retentate reservoir.

4. The module of claim 1 wherein the specific membrane area of the at least one channel is greater than about 80 cm$^{-1}$.

5. The module of claim 1 wherein the feed reservoir, the retentate reservoir and the permeate reservoir are juxtaposed along a centrifugal acceleration vector, the retentate reservoir interposed between the feed reservoir and the permeate reservoir.

6. The module of claim 1 further comprising:
a housing including the separation element; and
wherein the permeate reservoir is disposed within the housing.

7. A module for the filtration of a liquid sample comprising:
a separation element comprising at least one flow channel having a flow channel inlet, a wall having a surface comprising a filtration membrane; and a hydrophobic vent affixed to the channel distally from the inlet;
a feed reservoir fluidly coupled to the flow channel inlet;
a permeate reservoir fluidly coupled to the separation element;
wherein a specific membrane area of the at least one flow channel is greater than about 80 cm$^{-1}$; and
wherein a dimensionless length of the at least one flow channel is greater than about 2,000.

8. The module of claim 7 wherein the at least one flow channel including the filtration membrane is disposed within the permeate reservoir.

9. The module of claim 8 wherein the membrane is disposed on the outside surface of the flow channel.

10. A method for filtering a liquid sample comprising:
supplying a predetermined volume of the liquid sample into a feed reservoir of a separation module comprising:
a separation element having at least one flow channel having an inlet, an outlet and surface comprising a filtration membrane;
the feed reservoir fluidly coupled to the channel inlet;
a retentate reservoir fluidly coupled to the channel outlet;
a permeate reservoir fluidly coupled to the separation element;
wherein the ratio of the membrane area of the separation element to the volume of the feed reservoir is greater than about 2 cm$^{-1}$;
inducing the tangential flow of the liquid sample in the at least one flow channel by applying a first pressure differential between the feed reservoir and retentate reservoir; and
inducing the permeation of a portion of the liquid sample through the filtration membrane into the permeate reservoir by applying a second pressure differential between one of:
the retentate reservoir and permeate reservoir;
the feed reservoir and permeate reservoir.

11. The method of claim 10 further comprising independently controlling TCP and TMP by controlling the first and second pressure differentials independently of each other.

12. The method of claim 10 further comprising recovering a non-permeating fraction of the liquid sample, the step comprising:
substantially dissipating the first and second pressure differentials before fully consuming the liquid sample in the feed reservoir to stop permeation and tangential flow in the separation module; and
displacing the residual liquid sample within the channel by applying a third pressure differential between the feed and retentate reservoirs to induce flow of the liquid sample into the retentate reservoir.

13. The method of claim 10 further comprising recovering a non-permeating fraction of the liquid sample, the step comprising:
substantially consuming the liquid sample in the feed reservoir; and
substantially dissipating the first and second pressure differentials to stop permeation and tangential flow in the separation module.

14. The method of claim 13 further comprising:
inducing reverse permeation by applying a third pressure differential between the permeate and retentate reservoirs to induce flow of the liquid sample into the retentate reservoir; and
displacing the residual liquid sample within the channel; and
withdrawing the retentate from the retentate reservoir.

15. The method of claim 13 further comprising:
introducing a buffer to the feed reservoir;
displacing the residual liquid sample within the channel by applying a third pressure differential between the feed and retentate reservoirs to induce flow of the liquid sample into the retentate reservoir.

16. The method of claim 10 further comprising applying the first pressure differential and applying the second pressure differential substantially simultaneously.

17. A method for filtering a liquid sample comprising:
supplying a predetermined volume of liquid sample into a feed reservoir of a separation module comprising:
a separation element having at least one flow channel having an inlet and a surface comprising a filtration membrane;
the feed reservoir fluidly coupled to the channel inlet;
a permeate reservoir disposed adjacent the channel surface;
a hydrophobic vent affixed to the channel distally from the inlet;
wherein the specific membrane area of the at least one channel is greater than about 80 cm$^{-1}$;
inducing tangential flow within the flow channel and the permeation of a portion of the liquid sample through the filtration membrane into the permeate reservoir by applying a pressure differential between the feed reservoir and permeate reservoir; and
inducing the flow of the liquid sample in the at least one flow channel by venting the flow channel.

18. The method of claim 17 further comprising:
recovering a non-permeating fraction of the liquid sample, the step comprising:
substantially consuming the liquid sample in the feed reservoir; and
substantially dissipating the pressure differential to stop permeation and tangential flow in the separation module.

19. The method of claim 18 further comprising:
inducing a pressure differential between the vent and the feed reservoir to induce the infiltration of gas into the flow channel and displacing the residual liquid within the channel volume towards the feed reservoir; and
withdrawing the non-permeating fraction of the liquid sample from the feed reservoir.

20. A module for the filtration of a liquid sample comprising:
a separation element comprising at least one flow channel having a flow channel outlet, a wall having a surface comprising a filtration membrane;
a feed reservoir fluidly coupled to the flow channel;
a permeate reservoir fluidly coupled to the separation element; and
wherein the at least one flow channel is disposed within the feed reservoir;
wherein the filtration membrane is disposed on the outside surface of the flow channel;
wherein the ratio of the membrane area of the separation element to the volume of the feed reservoir is greater than about 2 $cm^{-1}$;
wherein the specific membrane area of the at least one flow channel is greater than about 80 $cm^{-1}$.

* * * * *